(12) United States Patent
Rivas et al.

(10) Patent No.: US 10,352,904 B2
(45) Date of Patent: *Jul. 16, 2019

(54) ACOUSTIC RESONATOR DEVICES AND METHODS PROVIDING PATTERNED FUNCTIONALIZATION AREAS

(71) Applicant: Qorvo US, Inc., Greensboro, NC (US)

(72) Inventors: Rio Rivas, Bend, OR (US); John Belsick, Bend, OR (US); Matthew Ryder, Bend, OR (US)

(73) Assignee: QORVO US, INC., Greensboro, NC (US)

( * ) Notice: Subject to any disclaimer, the term of this patent is extended or adjusted under 35 U.S.C. 154(b) by 71 days.

This patent is subject to a terminal disclaimer.

(21) Appl. No.: 15/334,511

(22) Filed: Oct. 26, 2016

(65) Prior Publication Data

US 2017/0117871 A1   Apr. 27, 2017

Related U.S. Application Data

(60) Provisional application No. 62/246,302, filed on Oct. 26, 2015.

(51) Int. Cl.
  *G01N 29/036*  (2006.01)
  *H03H 9/17*    (2006.01)
  *H03H 3/02*    (2006.01)

(52) U.S. Cl.
  CPC ............ *G01N 29/036* (2013.01); *H03H 3/02* (2013.01); *H03H 9/175* (2013.01); *G01N 2291/0426* (2013.01)

(58) Field of Classification Search
  CPC .................................................. G01N 29/036
  (Continued)

(56) References Cited

U.S. PATENT DOCUMENTS

| 4,640,756 A | 2/1987 | Wang et al. |
| 6,320,295 B1 | 11/2001 | McGill et al. |

(Continued)

FOREIGN PATENT DOCUMENTS

| EP | 2 204 641 A1 | 7/2010 |
| WO | WO 2006/063437 A1 | 6/2006 |

(Continued)

OTHER PUBLICATIONS

U.S. Appl. No. 15/293,063, filed Oct. 13, 2016, McCarron et al.

(Continued)

*Primary Examiner* — Joseph Chang
(74) *Attorney, Agent, or Firm* — Mueting, Raasch & Gebhardt, P.A.

(57) ABSTRACT

A micro-electrical-mechanical system (MEMS) resonator device includes a top side electrode overlaid with an interface layer including a material having a surface (e.g., gold or other noble metal, or a hydroxylated oxide) that may be functionalized with a functionalization (e.g., specific binding or non-specific binding) material. The interface layer and/or an overlying blocking material layer are precisely patterned to control locations of the interface layer available to receive a self-assembled monolayer (SAM), thereby addressing issues of misalignment and oversizing of a functionalization zone that would arise by relying solely on microarray spotting. Atomic layer deposition may be used for deposition of the interface layer and/or an optional hermeticity layer. Sensors and microfluidic devices incorporating MEMS resonator devices are also provided.

20 Claims, 9 Drawing Sheets

(58) Field of Classification Search
USPC .......................................................... 331/154
See application file for complete search history.

(56) References Cited

U.S. PATENT DOCUMENTS

| | | | |
|---|---|---|---|
| 7,468,608 | B2 | 12/2008 | Feucht et al. |
| 8,409,875 | B2 | 4/2013 | Johal et al. |
| 8,448,494 | B2 | 5/2013 | Mastromatteo et al. |
| 2005/0148065 | A1 | 7/2005 | Zhang et al. |
| 2006/0125489 | A1 | 6/2006 | Feucht et al. |
| 2007/0210349 | A1 | 9/2007 | Lu et al. |
| 2011/0121916 | A1 | 5/2011 | Barber et al. |
| 2012/0280758 | A1 | 11/2012 | Jaakkola et al. |
| 2012/0319790 | A1 | 12/2012 | Nakamura |
| 2013/0063227 | A1 | 3/2013 | Burak et al. |
| 2015/0293060 | A1 | 10/2015 | Jacobsen |
| 2017/0110300 | A1 | 4/2017 | McCarron et al. |
| 2017/0134001 | A1 | 5/2017 | Belsick et al. |
| 2018/0034438 | A1 | 2/2018 | Ryder et al. |
| 2018/0048280 | A1 | 2/2018 | Ryder et al. |

FOREIGN PATENT DOCUMENTS

| | | |
|---|---|---|
| WO | WO 2007/123539 A1 | 11/2007 |
| WO | PCT/US2016/058745 | 10/2016 |
| WO | PCT/US2016/058749 | 10/2016 |

OTHER PUBLICATIONS

U.S. Appl. No. 15/334,528, filed Oct. 26, 2016, Belsick et al.
U.S. Appl. No. 15/334,459, filed Oct. 26, 2016, Ryder et al.
U.S. Appl. No. 15/334,482, filed Oct. 26, 2016, Ryder et al.
U.S. Appl. No. 62/252,402, filed Nov. 6, 2015, Belsick et al.
U.S. Appl. No. 62/367,211, filed Jul. 27, 2016, Ryder et al.
U.S. Appl. No. 62/373,668, filed Aug. 11, 2016, Ryder et al.
International Patent Application No. PCT/US2016/058745, filed Oct. 26, 2016; International Search Report / Written Opinion dated Feb. 1, 2017; 13 pages.
International Patent Application No. PCT/US2016/058749, filed Oct. 26, 2016, International Search Report / Written Opinion dated Apr. 20, 2017; 16 pages.
Bjurström, et al., "Design and Fabrication of Temperature Compensated Liquid FBAR Sensors," *2006 IEEE Ultrasonics Symposium*, Oct. 2-6, 2006, pp. 894-897.
Chen, et al., "The Liquid Sensor Using Thin Film Bulk Acoustic Resonator with C-Axis Tilted AlN Films", 2013, *Journal of Nanomaterials*, vol. 2013, Article ID 245095, 8 pages.
Choi, et al., "A regenerative biosensing surface in microfluidics using electrochemical desorption of short-chain self-assembled monolayer", *Microfluidics and Nanofluidics*, 2009, Springer-Verlag, 7(6): 9 pages. Published online Apr. 10, 2009.
Ferrari, et al., Chapter 2, "Overview of Acoustic-Wave Microsensors", *Piezoelectric Transducers and Applications*, Springer-Verlag, Berlin Heidelberg, 2008, pp. 39-62.
Garcia-Gancedo, et al., "AlN-based BAW resonators with CNT electrodes for gravimetric biosensing", Dec. 15, 2011, *Sensors and Actuators B: Chemical*, 160(1): 1386-1393.
Hohmann, et al., "Surface Acoustic Wave (SAW) Resonators for Monitoring Conditioning Film Formation", 2015, *Sensors*, 15(5):11873-11888. Published online May 21, 2015.
Jiang, et al., "Electrochemical Desorption of Self-Assembled Monolayers Noninvasively Releases Patterned Cells from Geometrical Confinements", Nov. 26, 2002, *J. Am. Chem. Soc.*, 2003(125):2366-2367.
Luo, et al., Chapter 21, "Acoustic Wave Based Microfluidics and Lab-on-a-Chip," *Modeling and Measurement Methods for Acoustic Waves and or Acoustic Microdevices*, InTech, Aug. 28, 2013, pp. 515-556.
Mecca, "From Quartz Crystal Microbalance to Fundamental Principles of Mass Measurements", 2005, *Analytical Letters*, 38:753-767.

Onen, et al., "Surface Modification on Acoustic Wave Biosensors for Enhanced Specificity," 2012, *Sensors*, 12(9):12317-12328. Published online Sep. 10, 2012.
Plueddemann, *Silane Coupling Agents*, Springer Science+Business Media, New York, New York, 1991, p. 31.
Tencer, et al., "A contact angle and ToF-SIMS study of SAM-thiol interactions on polycrystalline gold", Feb. 15, 2011, *Applied Surface Science*, 257(9):4038-4043. Published online Dec. 4, 2010.
Villa-López, et al., "Design and modelling of solidly mounted resonators for low-cost particle sensing", 2016, *Measurement Science and Technology*, 27(2): 13 pages. Published online Dec. 15, 2015.
Ward, et al., "Radial Mass Sensitivity of the Quartz Crystal Microbalance in Liquid Media", May 1, 1991, *Analytical Chemistry*, 63(9):886-890.
Wiley, et al., "Rapid Degeneration of Alkanethiol-Based Self-Assembled Monolayers on Gold in Ambient Laboratory Conditions", Aug. 3, 2004, *Surface Science*, Preprint submitted to Elsevier Science, 576(1): 23 pages.
Wingqvist, et al., "Shear mode AlN thin film electro-acoustic resonant sensor operation in viscous media", 2007, *Sensors and Actuators B*, 123:466-473 Published online Nov. 2, 2006.
Yu, et al., "Ultra Temperature-Stable Bulk-Acoustic-Wave Resonators with $SiO_2$ Compensation. Layer," Oct. 2007, *IEEE Transactions on Ultrasonics, Ferroelectrics, and Frequency Control*, 54(10):2102-2109.
Yuan, et al., "A Method for Removing Self-Assembled Monolayers on Gold", 2008, *Langmuir*, 24(16):8707-8710. Published online Jun. 27, 2008.
Zhang, et al., "A single-chip biosensing platform integrating FBAR sensor with digital microfluidic device", *2014 IEEE International Ultrasonics Symposium Proceedings*, 2014, 3 pages.
Qorvo US, Inc., "Summary of Sales Activity of Predecessor to Applicant Concerning Tilted C-Axis Aluminum Nitride Products," Unpublished, Jan. 10, 2017, 1 page.
Canaria, Christie A. et al., "Formation and removal of alkylthiolate self-assembled monolayers on gold in aqueous solutions," Lab on a Chip, vol. 6, No. 2, 2006, pp. 289-295.
Corso, Christopher et al., "Development of a Simple Inexpensive Bulk Acoustic Wave (BAW) Nanosensor for Cancer Biomarkers: Detection of Secreted Sonic Hedgehog from Prostate Cancer Cells," Abstract #8866, Winship Cancer Institute, Emory University, Georgia Institute of Technology, Oct. 2012, 1 page.
Glass, Nick R. et al., "Organosilane deposition for microfluidic applications," Biomicrofluidics, vol. 5, No. 3, Aug. 16, 2011, pp. 036501-1 to 036501-7.
Groner, M. D. et al., "Gas diffusion barriers on polymers using $Al_2O_3$ atomic layer deposition," Applied Physics Letters, vol. 88, Jan. 31, 2006, pp. 051907-1 to 051907-3.
Link, Mathias, "Study and realization of shear wave mode solidly mounted film bulk acoustic resonators (FBAR) made of c-axis inclined zinc oxide (ZnO) thin films: application as gravimetric sensors in liquid environments," Université Henri Poincaré-Nancy I, Thesis, Sep. 14, 2006, 225 pages.
Love, J. Christopher et al., "Self-Assembled Monolayers of Thiolates on Metals as a Form of Nanotechnology," Chemical Reviews, vol. 105, No. 4, Mar. 25, 2005, pp. 1103-1169.
Mehdizadeh, Emad et al., "Microelectromechanical disk resonators for direct detection of liquid-phase analytes," Sensors and Actuators A: Physical, vol. 216, Sep. 1, 2014, pp. 136-141.
Meyer, Jens et al., "$Al_2O_3/ZrO_2$ Nanolaminates as Ultrahigh Gas-Diffusion Barriers—A Strategy for Reliable Encapsulation of Organic Electronics," Advanced Materials, vol. 21, 2009, pp. 1845-1849.
Milyutin, Evgeny, "Theoretical and Experimental Study of Piezoelectric Modulated AlN Thin Films for Shear Mode BAW Resonators," EPFL, Thesis No. 5113, Nov. 4, 2011, 109 pages.
Montagut, Yeison et al., "QCM Technology in Biosensors," Biosensors—Emerging Materials and Applications, Chapter 9, 2011, INTECH Open Access Publisher, pp. 153-178.
Mooney, J. F. et al., "Patterning of functional antibodies and other proteins by photolithography of silane monolayers," Proceedings of the National Academy of Sciences, vol. 93, No. 22, Oct. 29, 1996, pp. 12287-12291.

(56) References Cited

OTHER PUBLICATIONS

Munir, Farasat, "A Fast, Scalable Acoustic Resonator-Based Biosensor Array System for Simultaneous Detection of Multiple Biomarkers," Thesis, Georgia Institute of Technology, Dec. 2012, 160 pages.
Muskal, Nechama et al., "The Electrochemistry of Thiol Self-Assembled Monolayers (SAMs) on a Hanging Mercury Drop Electrode (HMDE)," Current Separations, vol. 19, No. 2, 2000, pp. 49-54.
Nirschl, Martin et al., "CMOS-Integrated Film Bulk Acoustic Resonators for Label-Free Biosensing," Sensors, vol. 10, No. 5, Apr. 27, 2010, pp. 4180-4193.
Ye, Tao et al., "Photoreactivity of Alkylsiloxane Self-Assembled Monolayers on Silicon Oxide Surfaces," Langmuir, vol. 17, No. 15, Jun. 21, 2001, pp. 4497-4500.
Zhang, X. et al., "Excimer laser ablation of thin gold films on a quartz crystal microbalance at various argon background pressures," Applied Physics A, vol. 64, No. 6, Jun. 1997, pp. 545-552.
Zhou, Yan et al., "Interfacial Structures and Properties of Organic Materials for Biosensors: An Overview," Sensors, vol. 12, Nov. 6, 2012, pp. 15036-15062.
Oliver Brand et al., Resonant MEMS, Wiley, ISBN-13: 9783527335459, Apr. 22, 2015. Chap. 15, Resonant MEMS Chemical Sensors.†
Lange, Kerstin, Bastian E. Rapp, and Michael Rapp. "Surface acoustic wave biosensors: a review." Analytical and bioanalytical chemistry 391.5 (2008): 1509-1519.†
Voiculescu, Ioana, and Anis Nurashikin Nordin. "Acoustic wave based MEMS devices for biosensing applications." Biosensors and Bioelectronics 33.1 (2012): 1-9.†

† cited by third party

10,352,904 B2

ACOUSTIC RESONATOR DEVICES AND METHODS PROVIDING PATTERNED FUNCTIONALIZATION AREAS

STATEMENT OF RELATED APPLICATIONS

This application is a non-provisional of U.S. Provisional Patent Application No. 62/246,302 filed on Oct. 26, 2015, the disclosure of which is hereby incorporated by reference herein in its entirety. Subject matter disclosed herein also relates to the following three U.S. patent applications each filed or to be filed on Oct. 26, 2016: (1) U.S. patent application Ser. No. 15/334,528, entitled "Acoustic Resonator Devices and Fabrication Methods Providing Hermeticity and Surface Functionalization;" (2) U.S. patent application Ser. No. 15/334,482, entitled "Acoustic Resonator Devices and Methods with Noble Metal Layer for Functionalization;" and (3) U.S. patent application Ser. No. 15/334,459, entitled "Acoustic Resonator Device with Controlled Placement of Functionalization Material;" wherein the contents of the foregoing three U.S. patent applications are hereby incorporated by reference as if set forth fully herein.

TECHNICAL FIELD

The present disclosure relates to acoustic resonator devices, including acoustic wave sensors and microfluidic devices suitable for biosensing or biochemical sensing applications.

BACKGROUND

A biosensor (or biological sensor) is an analytical device including a biological element and a transducer that converts a biological response into an electrical signal. Certain biosensors involve a selective biochemical reaction between a specific binding material (e.g., an antibody, a receptor, a ligand, etc.) and a target species (e.g., molecule, protein, DNA, virus, bacteria, etc.), and the product of this highly specific reaction is converted into a measurable quantity by a transducer. Other sensors may utilize a non-specific binding material capable of binding multiple types or classes of molecules or other moieties that may be present in a sample, such as may be useful in chemical sensing applications. The term "functionalization material" may be used herein to generally relate to both specific and non-specific binding materials. Transduction methods may be based on various principles, such as electrochemical, optical, electrical, acoustic, and so on. Among these, acoustic transduction offers a number of potential advantages, such as being real time, label-free, and low cost, as well as exhibiting high sensitivity.

An acoustic wave device employs an acoustic wave that propagates through or on the surface of a piezoelectric material, whereby any changes to the characteristics of the propagation path affect the velocity and/or amplitude of the wave. Presence of functionalization material embodied in a specific binding material along an active region of an acoustic wave device permits a specific analyte to be bound to the specific binding material, thereby altering the mass being vibrated by the acoustic wave and altering the wave propagation characteristics (e.g., velocity, thereby altering resonance frequency). Changes in velocity can be monitored by measuring the frequency, magnitude, or phase characteristics of the sensor, and can be correlated to a physical quantity being measured.

In the case of a piezoelectric crystal resonator, an acoustic wave may embody either a bulk acoustic wave (BAW) propagating through the interior of a substrate, or a surface acoustic wave (SAW) propagating on the surface of the substrate. SAW devices involve transduction of acoustic waves (commonly including two-dimensional Rayleigh waves) utilizing interdigital transducers along the surface of a piezoelectric material, with the waves being confined to a penetration depth of about one wavelength. In a BAW device, three wave modes can propagate, namely, one longitudinal mode (embodying longitudinal waves, also called compressional/extensional waves), and two shear modes (embodying shear waves, also called transverse waves), with longitudinal and shear modes respectively identifying vibrations where particle motion is parallel to or perpendicular to the direction of wave propagation. The longitudinal mode is characterized by compression and elongation in the direction of the propagation, whereas the shear modes consist of motion perpendicular to the direction of propagation with no local change of volume. Longitudinal and shear modes propagate at different velocities. In practice, these modes are not necessarily pure modes as the particle vibration, or polarization, is neither purely parallel nor purely perpendicular to the propagation direction. The propagation characteristics of the respective modes depend on the material properties and propagation direction respective to the crystal axis orientations. The ability to create shear displacements is beneficial for operation of acoustic wave devices with fluids (e.g., liquids) because shear waves do not impart significant energy into fluids.

Certain piezoelectric thin films are capable of exciting both longitudinal and shear mode resonance, such as hexagonal crystal structure piezoelectric materials including (but not limited to) aluminum nitride (AlN) and zinc oxide (ZnO). To excite a wave including a shear mode using a piezoelectric material layer arranged between electrodes, a polarization axis in a piezoelectric thin film must generally be non-perpendicular to (e.g., tilted relative to) the film plane. In biological sensing applications involving liquid media, the shear component of the resonator is used. In such applications, piezoelectric material may be grown with a c-axis orientation distribution that is non-perpendicular relative to a face of an underlying substrate to enable a BAW resonator structure to exhibit a dominant shear response upon application of an alternating current signal across electrodes thereof.

Typically, BAW devices are fabricated by micro-electro-mechanical systems (MEMS) fabrication techniques owing to the need to provide microscale features suitable for facilitating high frequency operation. In the context of biosensors, functionalization materials (e.g., specific binding materials; also known as bioactive probes or agents) may be deposited on sensor surfaces by microarray spotting (also known as microarray printing) using a microarray spotting needle. Functionalization materials providing non-specific binding utility (e.g., permitting binding of multiple types or species of molecules) may also be used in certain contexts, such as chemical sensing. Unfortunately, dimensional tolerances for microarray spotting are larger than dimensional tolerances enabled by MEMS fabrication techniques. An excess of specific binding material may reduce sensor response, such as by impairing a lower limit of detection. Separately, an excess of exposed non-specific binding material may lead to undesirable attachment of analyte when a device is in use. Although localized chemical or biological blocking techniques (e.g., using blocking buffers or proteins, such as bovine serum albumin (BSA), polyethylene oxide (PEO), or ethanolamine) could potentially be used to prevent or reduce non-specific binding, such blocking may require cumbersome empirical testing and may complicate device manufacturing. Moreover, the ability to stably operate BAW resonators in the presence of liquid may be limited, particularly for BAW resonators utilizing electrodes composed of reactive metals (e.g., aluminum or aluminum alloy) that are susceptible to corrosion when contacted with liquid. Hypothetical application of material over such electrodes must be carefully considered to avoid excess thickness that could dampen acoustic vibration and result in degraded performance. Surface compatibility of functionalization (e.g., specific binding) materials in the vicinity of such electrodes is also a concern, as is cost-effective and repeatable manufacturing.

Accordingly, there is a need for acoustic resonator devices suitable for operation in the presence of liquid for biosensing or biochemical sensing applications without negatively impacting device performance.

SUMMARY

The present disclosure provides a micro-electrical-mechanical system (MEMS) resonator device arranged on a substrate, the MEMS resonator device including a piezoelectric material layer, an interface layer, and a self-assembled monolayer (SAM) suitable for functionalization (e.g., by receiving at least one functionalization material) arranged over at least a portion of an active region of the device, wherein less than an entirety of the piezoelectric material layer is overlaid with interface layer material that is available to receive a SAM. In certain embodiments, the interface layer is arranged over less than an entirety of the piezoelectric material layer, or a patterned blocking layer (e.g., at least one of silicon nitride [$Si_3N_4$], silicon carbide [SiC], photoresist (e.g., including but not limited to SU-8), polyimide, parylene, or poly (ethylene glycol) [PEG]) is arranged over at least a portion of the interface layer, whereby presence of the patterned blocking material renders a portion of the interface layer unavailable to receive a SAM.

Deposition techniques such as atomic layer deposition (ALD), chemical vapor deposition (CVD), or physical vapor deposition (PVD) may be used in conjunction with one or more masks (e.g., photolithographic masks) to pattern the interface layer over at least certain portions of a MEMS resonator device (e.g., less than an entirety of a MEMS resonator device in certain embodiments), including at least a portion of an active region. The interface layer may comprise a material including a hydroxylated oxide surface, or gold or another noble metal, suitable for attachment of an organosilane-based SAM. An interface layer comprising a hydroxylated oxide surface may receive a SAM comprising an organosilane material, or an interface layer comprising gold or another noble metal may receive a SAM comprising a thiol material. By pre-defining a patterned interface layer with a high dimensional tolerance, forming a SAM registered with the interface layer, and then applying a functionalization (e.g., specific binding or non-specific binding) material to the SAM, a higher dimensional tolerance may be achieved for positioning of the functionalization material than could be attained by microarray spotting alone. In this manner, misalignment and overprinting challenges of microarray spotting can be overcome by improved patterning of underlying layers (i.e., an interface layer and SAM) that may be used to dictate placement of functionalization material. In certain embodiments incorporating electrode materials subject to corrosion, a hermeticity layer may also be applied between a top side electrode and the interface layer, with the hermeticity layer serving to protect the top side electrode. Microfluidic devices incorporating MEMS resonator devices disclosed herein are further provided, as well as methods for forming MEMS resonator devices and microfluidic devices.

In one aspect, a micro-electrical-mechanical system (MEMS) resonator device includes a substrate; a bulk acoustic wave resonator structure arranged over at least a portion of the substrate, an interface layer, and a self-assembled monolayer (SAM). The bulk acoustic wave resonator structure includes a piezoelectric material, a top side electrode arranged over a portion of the piezoelectric material, and a bottom side electrode arranged between the piezoelectric material and the substrate, wherein a portion of the piezoelectric material is between the top side electrode and the bottom side electrode to form an active region. The interface layer is arranged over at least a portion of the active region, wherein less than an entirety of the piezoelectric material is overlaid with interface layer material that is available to receive a self-assembled monolayer (SAM). The SAM is arranged over at least a portion of the interface layer. In certain embodiments, the interface layer comprises a hydroxylated oxide surface, and the self-assembled monolayer comprises an organosilane material. In certain embodiments, the interface layer comprises gold or another noble metal, and the self-assembled monolayer comprises a thiol material.

In certain embodiments, the interface layer is arranged over less than an entirety of the piezoelectric material. In certain embodiments, a patterned blocking layer is arranged over at least one portion of the interface layer. Such a blocking layer preferably comprises a material to which a self-assembled monolayer (SAM) is substantially non-adherent. In certain embodiments, such a patterned blocking layer may comprise at least one of $Si_3N_4$, SiC, photoresist (e.g., SU-8), polyimide, parylene, or poly(ethylene glycol). In certain embodiments, patterns may be defined in a blocking layer via etching. In the case of a patterned blocking layer comprising silicon nitride [$Si_3N_4$], an underlying interface (e.g., $SiO_2$) layer is preferably engineered to take into account the relative etch rates of the blocking layer material (e.g., $Si_3N_4$) and the interface layer material (e.g., $SiO_2$) in a dry etch process such as reactive ion etch with sulfur hexafluoride [$SF_6$]. Presence of a patterned blocking layer eliminates the need for biological or chemical blocking of the SAM to prevent binding of functionalization material in undesired locations. In certain embodiments, at least one functionalization (e.g. specific binding or non-specific binding) material is arranged over at least a portion of the self-assembled monolayer, wherein at least a portion of the at least one functionalization material is registered with the active region. In certain embodiments, the interface layer comprises at least one of silicon dioxide [$SiO_2$], titanium dioxide [$TiO_2$], tantalum pentoxide [$Ta_2O_5$], hafnium oxide [$HfO_2$], or aluminum oxide [$Al_2O_3$]. In certain embodiments, the top side electrode comprises a non-noble metal, and the MEMS resonator device further comprises a hermeticity layer arranged between the interface layer and the top side electrode. In certain embodiments, the hermeticity layer comprises an oxide, a nitride, or an oxynitride dielectric material, and the hermeticity layer comprises a water vapor transmission rate of no greater than 0.1 (g/m²/day). In certain embodiments, the hermeticity layer comprises a thickness in a range of from about 5 nm to about 100 nm, from about 5 nm to about 50 nm, or from about 10 nm to about 25 nm, and the interface layer comprises a thickness in a range of from about 1 nm to about 50 nm, or from about 2 nm to about 20 nm, or from about 5 nm to about 15 nm. In certain embodiments, a blocking layer is patterned over a portion of at least one of the top side electrode or the piezoelectric material, wherein the blocking layer is non-overlapping with respect to the active region. In certain embodiments, the piezoelectric material comprises a hexagonal crystal structure piezoelectric material (e.g., aluminum nitride or zinc oxide) that comprises a c-axis having an orientation distribution that is predominantly non-parallel to (and may also be non-perpendicular to) normal of a face of the substrate. In certain embodiments, an acoustic reflector structure is arranged between the substrate and the bulk acoustic wave resonator structure, wherein the bulk acoustic wave resonator structure comprises a solidly mounted bulk acoustic wave resonator structure. In other embodiments, the substrate defines a recess, and the MEMS resonator device further comprises a support layer arranged between the bulk acoustic wave resonator structure and the recess, wherein the active region is arranged over at least a portion of the support layer and at least a portion of the recess, such as to form a film bulk acoustic wave resonator (FBAR) structure.

In certain embodiments, the self-assembled monolayer comprises an organosilane material. In certain embodiments, the top side electrode comprises a noble metal not overlaid with a hermeticity layer.

Certain embodiments are directed to a sensor comprising a MEMS resonator device as disclosed herein, and/or to a fluidic (e.g., microfluidic) device incorporating a MEMS resonator device as disclosed herein with a fluidic passage arranged to conduct a liquid to contact the at least one functionalization material.

In another aspect, a method for biological or chemical sensing includes supplying a fluid containing a target species into the fluidic passage of a fluidic device (e.g., a microfluidic device) as disclosed herein, wherein said supplying is configured to cause at least some of the target species to bind to the at least one functionalization material; inducing a bulk acoustic wave in the active region; and sensing a change in at least one of a frequency property, a magnitude property, or a phase property of the bulk acoustic wave resonator structure to indicate at least one of presence or quantity of target species bound to the at least one functionalization material.

In another aspect, a micro-electrical-mechanical system (MEMS) resonator device includes a substrate; a bulk acoustic wave resonator structure arranged over at least a portion of the substrate, and at least one functionalization material. The bulk acoustic wave resonator structure includes a piezoelectric material, a top side electrode arranged over a portion of the piezoelectric material, and a bottom side electrode arranged between the piezoelectric material and the substrate, wherein a portion of the piezoelectric material is arranged between the top side electrode and the bottom side electrode to form an active region. The at least one functionalization material is arranged over at least a portion of the active region, wherein less than an entirety of the piezoelectric material is overlaid with the at least one functionalization material. In certain embodiments, the piezoelectric material comprises a hexagonal crystal structure piezoelectric material (e.g., aluminum nitride or zinc oxide) that comprises a c-axis having an orientation distribution that is predominantly non-parallel to normal of a face of the substrate. In certain embodiments, one or more portions of the piezoelectric material may be overlaid with a hermeticity layer, an interface layer, a SAM, and/or a blocking material as disclosed herein. In certain embodiments, a sensor and/or a fluidic device as disclosed herein may include the foregoing MEMS resonator device.

In another aspect, a method for fabricating a micro-electrical-mechanical system (MEMS) resonator device includes multiple steps. One step includes forming a bulk acoustic wave resonator structure including a piezoelectric material, a top side electrode arranged over a portion of the piezoelectric material, and a bottom side electrode arranged between the piezoelectric material and a substrate, wherein a portion of the piezoelectric material is arranged between the top side electrode and the bottom side electrode to form an active region. Another step includes depositing an interface layer over at least a portion of the active region, and wherein less than an entirety of the piezoelectric material is overlaid with interface layer material (e.g., comprising a hydroxylated oxide surface, or comprising gold or another noble metal) available to receive a self-assembled monolayer (SAM). Another step includes forming a self-assembled monolayer over at least a portion of the interface layer, wherein at least a portion of the self-assembled monolayer is arranged over the active region.

In certain embodiments, the method further includes applying a patterned mask over at least a portion of the bulk acoustic wave resonator structure prior to the depositing of the interface layer. In certain embodiments, the method further includes depositing at least one functionalization material over at least a portion of the self-assembled monolayer, wherein the at least one functionalization material is registered with at least a portion of the active region. In certain embodiments, the depositing of the interface layer comprises at least one of chemical vapor deposition, atomic layer deposition, or physical vapor deposition. In certain embodiments, the top side electrode comprises a non-noble metal, and the method further comprises depositing a hermeticity layer between at least portions of the interface layer and the top side electrode, wherein the hermeticity layer comprises an oxide, a nitride, or an oxynitride dielectric material, and wherein the hermeticity layer comprises a water vapor transmission rate of no greater than 0.1 (g/m$^2$/day). In certain embodiments, the method further comprises depositing a patterned blocking layer over at least one portion of the interface layer. In certain embodiments, such a patterned blocking layer may comprise at least one of $Si_3N_4$, SiC, photoresist (e.g., SU-8), polyimide, parylene, or poly(ethylene glycol). In certain embodiments, the method further comprises forming at least one wall over a portion of the bulk acoustic wave resonator structure and defining a fluidic passage containing the active region. Preferably, the fluidic passage may be covered with a cover or cap layer.

In another aspect, any of the foregoing aspects, and/or various separate aspects and features as described herein, may be combined for additional advantage. Any of the various features and elements as disclosed herein may be combined with one or more other disclosed features and elements unless indicated to the contrary herein.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWINGS

The accompanying drawing figures incorporated in and forming a part of this specification illustrate several aspects of the disclosure, and together with the description serve to explain the principles of the disclosure.

DETAILED DESCRIPTION

Figure 1:
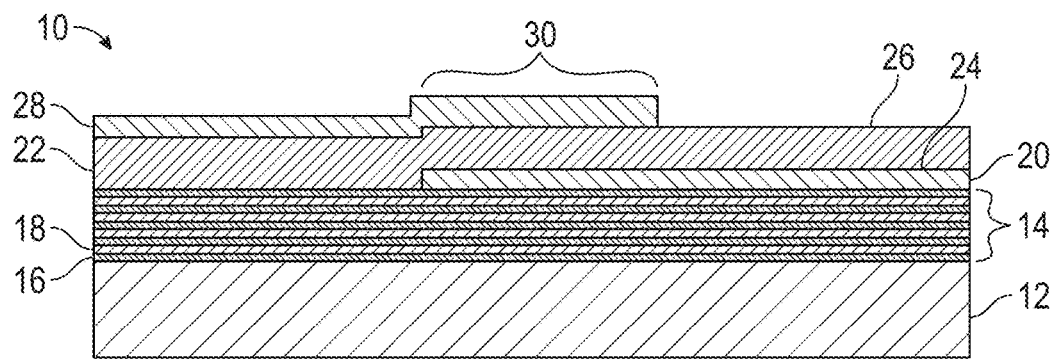
FIG. 1 is a schematic cross-sectional view of a portion of a MEMS resonator device useable with embodiments disclosed herein, including an active region with a piezoelectric material between overlapping portions of a top side electrode and a bottom side electrode.

Embodiments set forth below represent the necessary information to enable those skilled in the art to practice the invention and illustrate the best mode of practicing the invention. Upon reading the following description in light of the accompanying drawing figures, those skilled in the art will understand the concepts of the invention and will recognize applications of these concepts not particularly addressed herein. It should be understood that these concepts and applications fall within the scope of the disclosure and the accompanying claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

Relative terms such as "below" or "above" or "upper" or "lower" or "horizontal" or "vertical" may be used herein to describe a relationship of one element, layer, or region to another element, layer, or region as illustrated in the Figures. It will be understood that these terms and those discussed above are intended to encompass different orientations of the device in addition to the orientation depicted in the Figures.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof. As used herein, the terms "proximate" and "adjacent" as applied to a specified layer or element refer to a state of being close or near to another layer or element, and encompass the possible presence of one or more intervening layers or elements without necessarily requiring the specified layer or element to be directly on or directly in contact with the other layer or element unless specified to the contrary herein.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

The present disclosure relates in one aspect to a micro-electrical-mechanical system (MEMS) resonator device arranged on a substrate, the MEMS resonator device including a piezoelectric material, an interface layer, and a self-assembled monolayer (SAM) suitable for biological functionalization (e.g., by receiving at least one specific binding material) arranged over at least a portion of an active region of the device, wherein less than an entirety of the piezoelectric material is overlaid with interface layer material that is available to receive a self-assembled monolayer. In certain embodiments, the interface layer is arranged over less than an entirety of the piezoelectric material, or a patterned blocking layer (e.g., at least one of $Si_3N_4$, SiC, photoresist (e.g., SU-8), polyimide, parylene, or polyethylene glycol) is arranged over at least a portion of the interface layer whereby presence of the patterned blocking material renders a portion of the interface layer unavailable to receive a SAM. Deposition techniques such as atomic layer deposition (ALD), chemical vapor deposition (CVD), or physical vapor deposition (PVD) may be used in conjunction with one or more masks (e.g., photolithographic masks) to pattern the interface layer over selected portions (i.e., less than the entirety) of a MEMS resonator device, including at least a portion of an active region. The interface layer preferably comprises a material suitable for attachment of an organosilane-based SAM. By pre-defining a patterned interface layer with a high dimensional tolerance (i.e., either the interface layer itself, or by covering one or more regions of the interface layer with blocking material), forming a SAM registered with the interface layer, and then applying a functionalization (e.g., specific binding) material to the SAM, a higher dimensional tolerance may be achieved for positioning of the functionalization material than could be attained by microarray spotting alone. In this manner, alignment and overprinting challenges of microarray spotting can be overcome by improved patterning of underlying layers (i.e., an interface layer and SAM).

A preferred micro-electrical-mechanical system (MEMS) resonator device according to certain embodiments includes a substrate, a bulk acoustic wave resonator structure arranged over at least a portion of the substrate, an interface layer, and a self-assembled monolayer (SAM). In certain embodiments of the present disclosure, an interface layer is arranged over at least a portion of the active region but arranged over less than an entirety of a piezoelectric material, and the SAM being arranged over at least a portion of the interface layer. In other embodiments, an interface layer is provided over a larger area (optionally spanning over an entire piezoelectric material), and a patterned blocking layer (e.g., at least one of $Si_3N_4$, SiC, photoresist (e.g., SU-8), polyimide, parylene, or polyethylene glycol) is arranged over at least a portion of the interface layer, whereby presence of the patterned blocking material renders a portion of the interface layer unavailable to receive a SAM. In certain embodiments, the interface layer comprises a hydroxylated oxide surface, and the self-assembled monolayer comprises an organosilane material. In certain embodiments, the interface layer comprises gold or another noble metal, and the self-assembled monolayer comprises a thiol material.

FIG. 1 is a schematic cross-sectional view of a portion of a bulk acoustic wave MEMS resonator device that is devoid of overlying layers but useable with embodiments disclosed herein. The bulk acoustic wave MEMS resonator device 10 includes a substrate 12 (e.g., typically silicon or another semiconductor material), an acoustic reflector 14 arranged over the substrate 12, a piezoelectric material 22, and bottom and top side electrodes 20, 28. The bottom side electrode 20 is arranged along a portion of a lower surface 24 of the piezoelectric material 22 (between the acoustic reflector 14 and the piezoelectric material 22), and the top side electrode 28 is arranged along a portion of an upper surface 26 of the piezoelectric material 22. An area in which the piezoelectric material 22 is arranged between overlapping portions of the top side electrode 28 and the bottom side electrode 20 is considered the active region 30 of the resonator device 10. The acoustic reflector 14 serves to reflect acoustic waves and therefore reduce or avoid their dissipation in the substrate 12. In certain embodiments, an acoustic reflector 14 includes alternating thin layers 16, 18 of different materials (e.g., silicon oxicarbide [SiOC], silicon nitride [$Si_3N_4$], silicon dioxide [$SiO_2$], aluminum nitride [AlN], tungsten [W], and molybdenum [Mo]), optionally embodied in a quarter-wave Bragg mirror, deposited over the substrate 12. In certain embodiments, other types of acoustic reflectors may be used. Steps for forming the resonator device 10 may include depositing the acoustic reflector 14 over the substrate 12, followed by deposition of the bottom side electrode 20, followed by growth (e.g., via sputtering or other appropriate methods) of the piezoelectric material 22, followed by deposition of the top side electrode 28.

In certain embodiments, an interface layer is patterned or otherwise available to receive a SAM over an entirety of an active region of a MEMS resonator device, to permit a SAM and functionalization (e.g., specific binding) material applied over the interface layer to overlap the entire active region. In other embodiments, a blocking layer is patterned over an interface layer, or only a portion of the interface layer is otherwise available to receive a SAM, over only a portion of an active region, to permit the SAM and functionalization material applied over the interface layer to overlap only a portion of the active region.

In certain embodiments, photolithography may be used to promote patterning of interface material or blocking material over portions of a MEMS resonator device. Photolithography involves use of light to transfer a geometric pattern from a photomask to a light-sensitive chemical photoresist on a substrate, and is a process well known to those of ordinary skill in the semiconductor fabrication art. Typical steps employed in photolithography include wafer cleaning, photoresist application (involving either positive or negative photoresist), mask alignment, and exposure and development. After features are defined in photoresist on a desired surface, an interface layer may be patterned by etching in one or more gaps in a photoresist layer, and the photoresist layer may be subsequently removed (e.g., using a liquid photoresist stripper, by ashing via application of an oxygen-containing plasma, or another removal process).

In certain embodiments, an interface layer includes a hydroxylated oxide surface suitable for formation of an organosilane SAM layer. A preferred interface layer material including a hydroxylated oxide surface is silicon dioxide [$SiO_2$]. Alternative materials incorporating hydroxylated oxide surfaces for forming interface layers include titanium dioxide [$TiO_2$] and tantalum pentoxide [$Ta_2O_5$]. Other alternative materials incorporating hydroxylated oxide surfaces will be known to those skilled in the art, and these alternatives are considered to be within the scope of the present disclosure.

In other embodiments, an interface layer includes gold or another noble metal (e.g., ruthenium, rhodium, palladium, osmium, iridium, platinum, or silver) suitable for receiving a thiol-based SAM.

In certain embodiments incorporating electrode materials subject to corrosion, a hermeticity layer may also be applied between a top side electrode and the interface layer. A hermeticity layer may be unnecessary when noble metals (e.g., gold, platinum, etc.) are used for top side electrodes. If provided, a hermeticity layer preferably includes a dielectric material with a low water vapor transmission rate (e.g., no greater than 0.1 (g/$m^2$/day)). Following deposition of these layers, a SAM may be formed over the interface layer, with the SAM preferably including an organosilane material. The hermeticity layer protects a reactive electrode material (e.g., aluminum or aluminum alloy) from attack in corrosive liquid environments, and the locally patterned interface layer facilitates proper chemical binding of the SAM.

In certain embodiments, a hermeticity layer and/or an interface layer may be applied via one or more deposition processes such as atomic layer deposition (ALD), chemical vapor deposition (CVD), or physical vapor deposition (PVD). Of the foregoing processes, ALD is preferred for deposition of at least the hermeticity layer (and may also be preferable for deposition of the interface layer), due to its ability to provide excellent conformal coating with good step coverage over device features, so as to provide layer structures that are free of pinholes. Moreover, ALD is capable of forming uniformly thin layers that provide relatively little damping of acoustic vibrations that would otherwise result in degraded device performance. Adequacy of coverage is important for a hermeticity layer (if present) to avoid corrosion of the underlying electrode. If ALD is used for deposition of a hermeticity layer, then in certain embodiments a hermeticity layer may include a thickness in a range of from about 10 nm to about 25 nm. In certain embodiments, hermeticity layer thickness is about 15 nm, or from about 12 nm to about 18 nm. Conversely, if another process such as CVD is used, then a hermeticity layer may include a thickness in a range of from about 80 nm to about 150 nm or more, or in a range of from about 80 nm to about 120 nm. Considering both of the foregoing processes, hermeticity layer thicknesses may range from about 5 nm to about 150 nm. If ALD is used for deposition of an interface layer, then an interface layer may include a thickness in a range of from about 5 nm to about 15 nm. In certain embodiments, an interface layer may include a thickness of about 10 nm, or in a range of from about 8 nm to about 12 nm. Other interface layer thickness ranges and/or deposition techniques other than ALD may be used in certain embodiments. In certain embodiments, a hermeticity layer and an interface layer may be sequentially applied in a vacuum environment, thereby promoting a high-quality interface between the two layers.

If provided, a hermeticity layer may include an oxide, a nitride, or an oxynitride material serving as a dielectric material and having a low water vapor transmission rate (e.g., no greater than 0.1 (g/$m^2$/day)) according to certain embodiments. In certain embodiments, the hermeticity layer includes at least one of $Al_2O_3$ or SiN. In certain embodiments, the interface layer includes at least one of $SiO_2$, $TiO_2$, or $Ta_2O_5$. In certain embodiments, multiple materials may be combined in a single hermeticity layer, and/or a hermeticity layer may include multiple sublayers of different materials. Preferably, a hermeticity layer is further selected to promote compatibility with an underlying reactive metal (e.g., aluminum or aluminum alloy) electrode structure of an acoustic resonator structure. Although aluminum or aluminum alloys are frequently used as electrode materials in bulk acoustic wave resonators, various transition and post-transition metals can be used for such electrodes.

Following deposition of an interface layer (optionally arranged over an underlying hermeticity layer), a SAM is preferably formed over the interface layer. SAMs are typically formed by exposure of a solid surface to amphiphilic molecules with chemical groups that exhibit strong affinities for the solid surface. When an interface layer comprising a hydroxylated oxide surface is used, then organosilane SAM layers are particularly preferred for attachment to the hydroxylated oxide surface. Organosilane SAMs promote surface bonding through silicon-oxygen (Si—O) bonds. More specifically, organosilane molecules include a hydrolytically sensitive group and an organic group, and are therefore useful for coupling inorganic materials to organic polymers. An organosilane SAM may be formed by exposing a hydroxylated surface to an organosilane material in the presence of trace amounts of water to form intermediate silanol groups. These groups then react with free hydroxyl groups on the hydroxylated surface to covalently immobilize the organosilane. Examples of possible organosilane-based SAMs that are compatible with interface layers incorporating hydroxylated oxide surfaces include 3-glycidoxypropyltrimethoxysilane (GPTMS), 3-mercaptopropyltrimethoxysilane (MPTMS), 3-aminopropyltrimethoxysilane (APTMS), and octadecyltrimethoxysilane (OTMS), including their ethoxy- and chloro-variants. Additional silanes that may be used for SAMs include poly(ethylene glycol) (PEG) conjugated variants. Those skilled in the art will recognize that other alternatives exist, and these alternatives are considered to be within the scope of the present disclosure. An exemplary SAM may include a thickness in a range of at least 0.5 nm or more. Preferably, a SAM readily binds to the locally patterned interface layer, but does not readily bind to other adjacent material layers (e.g., a hermeticity layer, a piezoelectric material, and/or a blocking material layer).

When an interface layer comprising gold or another noble metal is used, then thiol-based (e.g., alkanethiol-based) SAM layers may be used. Alkanethiols are molecules with an alkyl chain as the back bone, a tail group, and a S—H head group. Thiols may be used on noble metal interface layers due to the strong affinity of sulfur for these metals. Examples of thiol-based SAMs that may be used include, but are not limited to, 1-dodecanethiol (DDT), 11-mercaptoundecanoic acid (MUA), and hydroxyl-terminated (hexaethylene glycol) undecanethiol (1-UDT). These thiols contain the same backbone, but different end groups—namely, methyl ($CH_3$), carboxyl (COOH), and hydroxyl-terminated hexaethylene glycol (HO—$(CH_2CH_2O)_6$) for DDT, MUA, and 1-UDT, respectively. In certain embodiments, SAMs may be formed by incubating gold surfaces in thiol solutions using a suitable solvent, such as anhydrous ethanol.

Following formation of a SAM, the SAM may be biologically functionalized, such as by receiving at least one functionalization (e.g., specific binding) material. In certain embodiments, specific binding materials may be applied on or over a SAM using a microarray spotting needle or other suitable methods. Since a SAM and an underlying interface layer are patterned (e.g., using photolithography for defining the interface layer) with a high dimensional tolerance over only a portion of a resonator structure (which includes a substrate), and the subsequently applied specific binding material preferably attaches only to the SAM, a higher dimensional tolerance may be achieved for positioning of the specific binding material than could be attained by microarray spotting alone. Examples of specific binding materials include, but are not limited to, antibodies, receptors, ligands, and the like. A specific binding material is preferably configured to receive a predefined target species (e.g., molecule, protein, DNA, virus, bacteria, etc.). A functionalization layer including specific binding material may include a thickness in a range of from about 5 nm to about 1000 nm, or from about 5 nm to about 500 nm. In certain embodiments, an array of different specific binding materials may be provided over different active areas of a multi-resonator device (i.e., a resonator device including multiple active areas), optionally in combination with one or more active areas that are devoid of specific binding materials to serve as comparison (or "reference") regions. In certain embodiments, a functionalization material may provide non-specific binding utility.

Certain embodiments are directed to a fluidic device including multiple bulk acoustic wave MEMS resonator structures as disclosed herein and including a fluidic passage (e.g., a channel, a chamber, or the like) arranged to conduct a liquid to contact at least one functionalization (e.g., specific binding) material arranged over at least one active region of the resonator structures. Such a device may be microfluidic in scale, and comprise at least one microfluidic passage (e.g., having at least one dimension, such as height and/or width, of no greater than about 500 microns, or about 250 microns, or about 100 microns). For example, following fabrication of bulk acoustic wave MEMS resonator structures and deposition of a SAM over portions thereof (optionally preceded by deposition of a hermeticity layer and an interface layer), a microfluidic device may be fabricated by forming one or more walls defining lateral boundaries of a microfluidic passage over a first bulk acoustic wave MEMS resonator structure with an active region thereof arranged along a bottom surface of the microfluidic passage, and then enclosing the microfluidic passage using a cover or cap layer that may define fluidic ports (e.g., openings) enabling fluid communication with the microfluidic passage. In certain embodiments, functionalization (e.g., specific binding) material may be pre-applied to the active region of a bulk acoustic wave MEMS resonator structure before formation of a microfluidic passage; in other embodiments, functionalization material may be applied over an active region of a bulk acoustic wave resonator structure following formation of the microfluidic passage.

Figure 2:
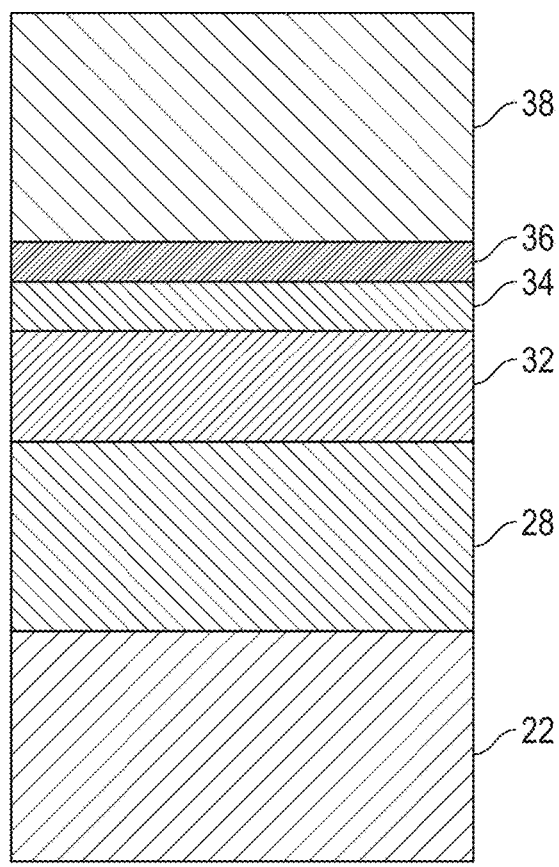
FIG. 2 is a schematic cross-sectional view of an upper portion of a MEMS resonator device according to one embodiment of the present disclosure, including a top side electrode overlaid with a hermeticity layer, an interface layer, a self-assembled monolayer, and a functionalization layer (e.g., specific binding material).

An example of a MEMS resonator device overlaid with multiple layers for providing biosensing utility according to one embodiment is provided in FIG. 2. FIG. 2 is a schematic cross-sectional view of an upper portion of a MEMS resonator device including a piezoelectric material 22 and a top side electrode 28, wherein at least the top side electrode 28 is overlaid with a hermeticity layer 32, an interface layer 34, a self-assembled monolayer 36, and a functionalization layer (e.g., specific binding material) 38. In certain embodiments, the MEMS resonator device includes a bulk acoustic wave resonator device, and the piezoelectric material 22 includes aluminum nitride or zinc oxide material that includes a c-axis having an orientation distribution that is predominantly non-parallel (and may also be non-perpendicular) to normal of a face of the substrate. Such a c-axis orientation distribution enables creation of shear displacements, which beneficially enable operation of the MEMS resonator device with liquids, such as in a sensor and/or microfluidic device. In certain embodiments, piezoelectric material includes a c-axis with a longitudinal orientation.

Methods for forming hexagonal crystal structure piezoelectric materials including a c-axis having an orientation distribution that is predominantly non-parallel to normal of a face of a substrate are disclosed in U.S. patent application Ser. No. 15/293,063 filed on Oct. 13, 2016, with the foregoing application hereby being incorporated by reference herein. Additional methods for forming piezoelectric materials having an inclined c-axis orientation are disclosed in U.S. Pat. No. 4,640,756 issued on Feb. 3, 1987, with the foregoing patent hereby being incorporated by reference herein.

Certain embodiments are directed to a fluidic device (e.g., a microfluidic device) including a MEMS resonator device as disclosed herein and including a fluidic passage (e.g., a channel, a chamber, or the like) arranged to conduct a liquid to contact at least one functionalization material. For example, following fabrication of a MEMS resonator device and deposition of an interface layer and a SAM over portions thereof (optionally preceded by deposition of a hermeticity layer), a microfluidic device may be fabricated by forming one or more walls defining lateral boundaries of a microfluidic channel preferably containing the active region of at least one acoustic resonator, followed by application of a cover or cap layer to enclose the microfluidic channel. In certain embodiments, functionalization (e.g., specific binding) material may be applied after formation of walls of a microfluidic channel, but prior to application of the cover or cap layer. Walls of a microfluidic channel may be formed of any suitable material, such as laser-cut "stencil" layers of thin polymeric materials and/or laminates, optionally including one or more self-adhesive surfaces (e.g., adhesive tape). Optionally such walls may be formed prior to deposition of a SAM layer, a functionalization layer, and/or blocking layers, with an SU-8 negative epoxy resist or other photoresist material. A cover or cap layer of a microfluidic device may be formed by defining ports (e.g., via laser cutting or water jet cutting) in a layer of an appropriate material (e.g., preferably a substantially inert polymer, glass, silicon, ceramic, or the like), and adhering the cover or cap layer to top surfaces of the walls.

Figure 3:
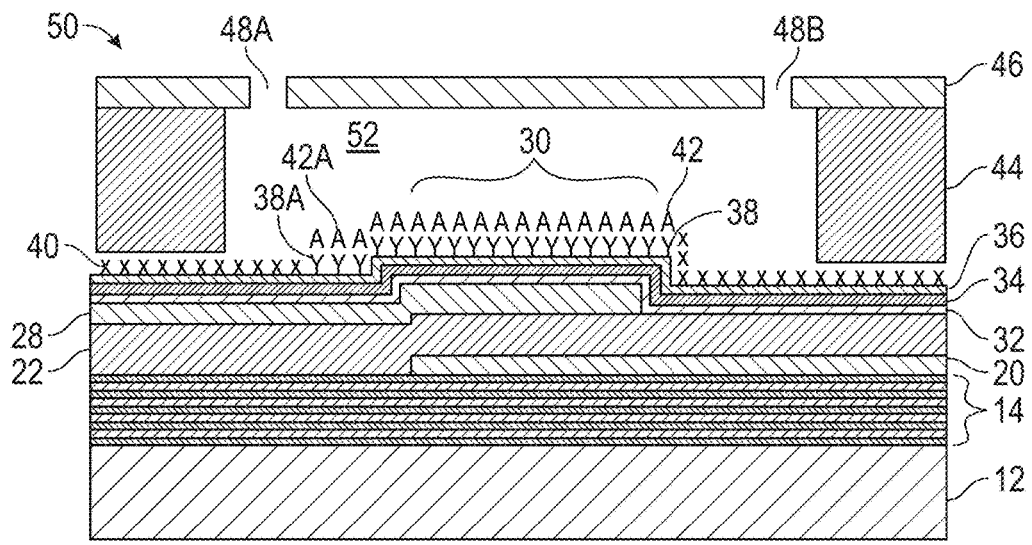
FIG. 3 is a schematic cross-sectional view of a microfluidic device incorporating a bulk acoustic wave MEMS resonator device including top side electrode and piezoelectric material surfaces overlaid with a hermeticity layer, an interface layer, a self-assembled monolayer (SAM) arranged over the interface layer, and functionalization (e.g., specific binding) material and blocking material arranged over first and second portions of the SAM, respectively, wherein the functionalization material extends beyond an active region of the MEMS resonator device.

As indicated previously herein, it may be difficult to achieve a high degree of alignment between functionalization material and an active region of a MEMS resonator device through reliance on microarray spotting. FIG. 3 is a schematic cross-sectional view of a microfluidic device 50 incorporating a bulk acoustic wave MEMS resonator device including top side electrode 28 and piezoelectric material 22 surfaces overlaid with a hermeticity layer 32, an interface layer 34, a self-assembled monolayer (SAM) 36 arranged over the interface layer 34, and functionalization (e.g., specific binding) material 38 and chemical or biological blocking material (e.g., a blocking buffer) 40 arranged over first and second (i.e., central and peripheral) portions of the SAM 36, respectively. The hermeticity layer 32, the interface layer 34, and the SAM 36 extend over substantially the entirety of a substrate 12; however, the chemical or biological blocking material 40 (which is non-coincident with an active region 30) locally prevents adhesion of functionalization material 38 to the interface layer 34.

The proper choice of a chemical or biological blocking material (e.g., blocking buffer) for a given analysis depends on the type of target species or analyte present in a sample. Various types of blocking buffers such as highly purified proteins, serum, or milk may be used to block free sites on a monolayer. Additional blockers include ethanolamine or polyethylene oxide (PEO) containing materials. An ideal blocking buffer would bind to all potential sites of nonspecific interaction away from an active region. To optimize a blocking buffer for a particular analysis, empirical testing may be used to determine signal-to-noise ratio. No single chemical blocking material is ideal for every situation, since each antibody-antigen pair has unique characteristics.

In FIG. 3, a target species 42 is bound to the functionalization material 38. The MEMS resonator device further includes the substrate 12, an acoustic reflector 14, and a bottom side electrode 20 arranged below the piezoelectric material 22. Walls 44 that are laterally displaced from the active region 30 extend upward (e.g., above the SAM 36) to define lateral boundaries of a microfluidic channel 52 containing the active region 30. If the walls 44 are formed on the SAM 36, the SAM 36 may promote adhesion of the walls 44. Such walls may be formed of any suitable material, such as a laser-cut "stencil" layer of thin polymeric materials and/or laminate materials, optionally including one or more self-adhesive surfaces (e.g. adhesive tape). Optionally such walls may be formed prior to deposition of a SAM, functionalization and blocking layers with an SU-8 negative epoxy resist or other photoresist material. A cover 46 defining fluidic ports 48A, 48B is further provided to provide an upper boundary for the microfluidic channel 52.

As shown in FIG. 3, a laterally extending portion 38A of the functionalization material 38 extends laterally beyond the active region 30 of the MEMS resonator device, and a portion 42A of the target species 42 is bound to the laterally extending portion 38A of the functionalization material 38. This laterally extending portion 38A of the functionalization material 38 constitutes excess functionalization (e.g., specific binding) material that may reduce sensor response, such as by impairing a lower limit of detection. Moreover, the excess functionalization material 38A is also arranged asymmetrically relative to the active region 30. The presence of excess functionalization material 38A misaligned with the active region 30 may be undesirable, giving rise to the subject matter of the present application in which a patterned interface layer with a high dimensional tolerance is applied over a MEMS resonator structure, a SAM is subsequently formed registered with the interface layer, and a functionalization (e.g., specific binding) material is applied to the SAM, as described in connection with various embodiments that follow.

Figure 4:
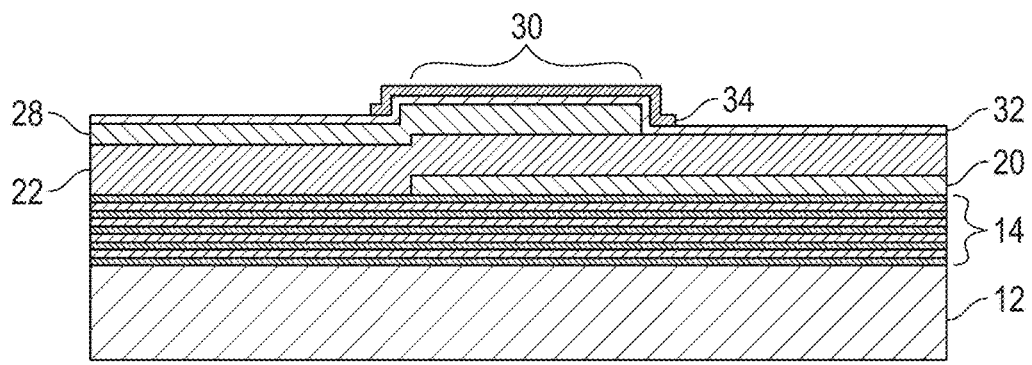
FIG. 4 is a schematic cross-sectional view of a portion of a MEMS resonator device including top side electrode and piezoelectric material surfaces overlaid with a hermeticity layer, and with an interface layer patterned over a portion of the hermeticity layer to cover an active region of the MEMS resonator device, according to one embodiment of the present disclosure.

FIG. 4 is a schematic cross-sectional view of a portion of a MEMS resonator device similar to the device of FIG. 1 (including a substrate 12, an acoustic reflector 14, a piezoelectric material 22, bottom and top side electrodes 20, 28), but with surfaces of the top side electrode 28 and the piezoelectric material 22 being overlaid with a hermeticity layer 32, and with an interface layer 34 patterned over a central portion of the hermeticity layer 32 to cover an active region 30 of the MEMS resonator device, according to one embodiment of the present disclosure. The interface layer 34 preferably comprises a hydroxylated oxide surface, or a gold or other noble metal, suitable for receiving a SAM. In certain embodiments, the interface layer 34 may be patterned over a portion of the MEMS resonator device (e.g., to cover only a portion of the substrate 12) using a photomask (not shown). As shown, the interface layer 34 may cover an entire horizontal top surface as well as (e.g., vertical) step surfaces of the top side electrode 28, but does not extend laterally a significant distance away from the active region 30.

Figure 5:
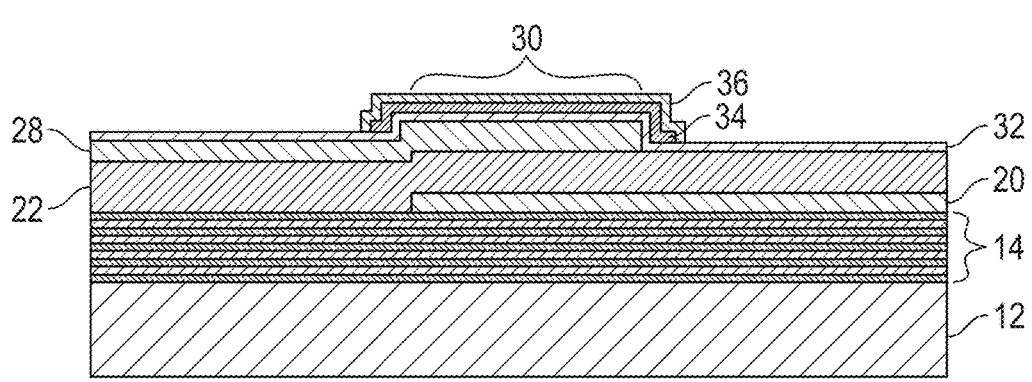
FIG. 5 is a schematic cross-sectional view of the MEMS resonator device portion of FIG. 4 following application of a self-assembled monolayer (SAM) over the interface layer to cover the active region of the MEMS resonator device, according to one embodiment of the present disclosure.

FIG. 5 is a schematic cross-sectional view of the MEMS resonator device portion of FIG. 4 following application of a self-assembled monolayer (SAM) 36 over the interface layer 34 to cover the active region 30 of the MEMS resonator device, according to one embodiment of the present disclosure. In certain embodiments, the SAM 36 comprises an organosilane material. The remaining elements of FIG. 5 are identical to those disclosed in connection with FIG. 4. Since the interface layer 34 is locally patterned over a central portion of the MEMS resonator device, the SAM 36 preferably adheres to the interface layer 34 (e.g., $SiO_2$) but not to the hermeticity layer 32 (e.g., SiN), less than an entirety of the piezoelectric material 22 is overlaid with interface layer material that is available to receive a SAM. Moreover, the need for a chemical or biological blocking material (e.g., material 40 as shown in FIG. 3) to prevent subsequent deposition of functionalization material 38 away from the active region 30 may be avoided.

Figure 6:
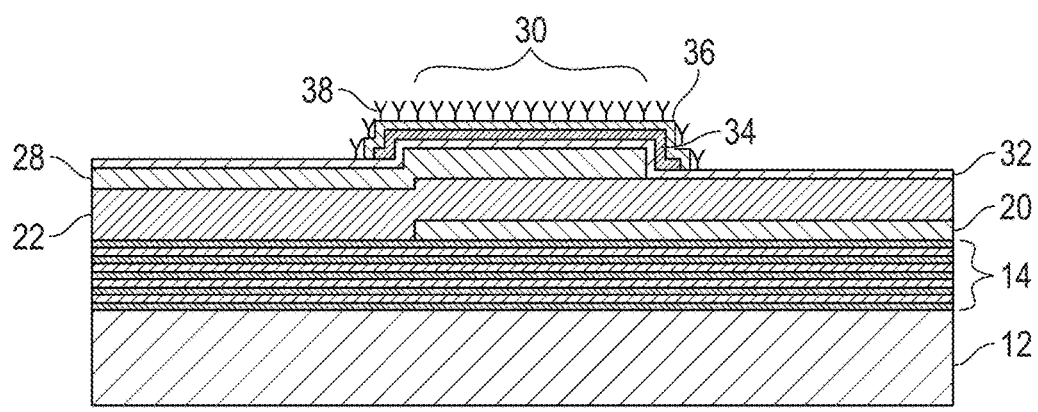
FIG. 6 is a schematic cross-sectional view of the MEMS resonator device portion of FIG. 5 following application of a functionalization (e.g., specific binding) material over the self-assembled monolayer (SAM) to cover the active region of the MEMS resonator device, according to one embodiment of the present disclosure.

FIG. 6 is a schematic cross-sectional view of the MEMS resonator device portion of FIG. 5 following application of a functionalization (e.g., specific binding) material 38 over the self-assembled monolayer (SAM) 36 (which is arranged over the interface layer 34) to cover the active region 30 of the MEMS resonator device, according to one embodiment of the present disclosure. The remaining elements of FIG. 6 are identical to those disclosed in connection with FIGS. 4 and 5. As shown, the functionalization material 38 covers an entire horizontal top surface as well as (e.g., vertical) step surfaces of the top side electrode 28, the SAM 36, and the interface layer 34, but does not extend laterally a significant distance away from the active region 30. The functionalization material 38 may be "overprinted" to ensure that the entire active region 30 is covered, and thereafter any excess functionalization material may be washed away. The zone where functionalization material 38 is present is therefore defined by the precise process step of patterning the interface layer 34, thereby addressing issues of misalignment and oversizing of a functionalization zone that would arise by relying solely on microarray spotting to determine placement of the functionalization material 38.

Figure 7:
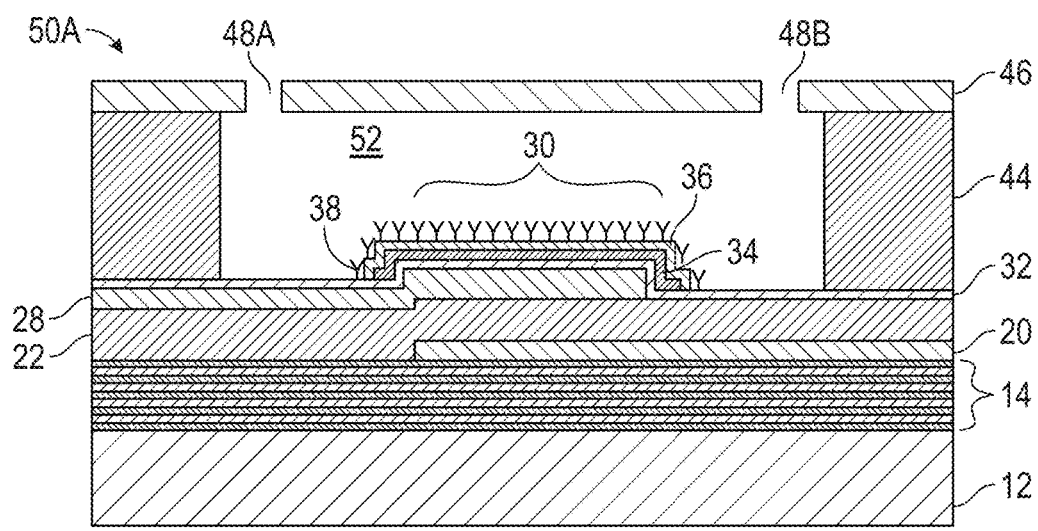
FIG. 7 is a schematic cross-sectional view of a microfluidic device incorporating a bulk acoustic wave MEMS resonator device according to FIG. 6, with walls defining lateral boundaries and with a cover or cap layer defining an upper boundary of a microfluidic channel containing the active region of the MEMS resonator device, according to one embodiment of the present disclosure.

FIG. 7 is a schematic cross-sectional view of a microfluidic device 50A incorporating a bulk acoustic wave MEMS resonator device according to FIG. 6, with walls 44 defining lateral boundaries and with a cover 46 defining an upper boundary of a microfluidic channel 52 containing an active region 30 of the MEMS resonator device, according to one embodiment of the present disclosure. The cover 46 defines fluidic ports 48A, 48B suitable to permit fluid (e.g., liquid) containing a target species to be introduced into the microfluidic channel 52. The MEMS resonator device includes a substrate 12, an acoustic reflector 14 arranged over the substrate 12, a piezoelectric material 22, and bottom and top side electrodes 20, 28 arranged under and over regions of the piezoelectric material 22, respectively. An area in which the piezoelectric material 22 is arranged between overlapping portions of the top side electrode 28 and the bottom side electrode 20 defines the active region 30. A hermeticity layer 32 is provided over an entirety of the top side electrode 28 and the piezoelectric material 22. An interface layer 34 is patterned over a central portion of the hermeticity layer 32 including the active region 30, and a SAM 36 is locally provided over the interface layer 34. As shown, functionalization material 38 is arranged over an entire horizontal top surface as well as (e.g., vertical) step surfaces of the top side electrode 28, the SAM 36, and the interface layer 34, but does not extend laterally a significant distance away from the active region 30. Preferably, fabrication of the microfluidic device 50A includes formation of a MEMS resonator according to FIG. 1, followed by deposition of the hermeticity layer 32, localized deposition of the interface layer 34 and formation of the SAM 36 over the active region 30, formation of the walls 44, deposition of the functionalization material 38 over the SAM 36, and application of the cover 46.

Figure 8:
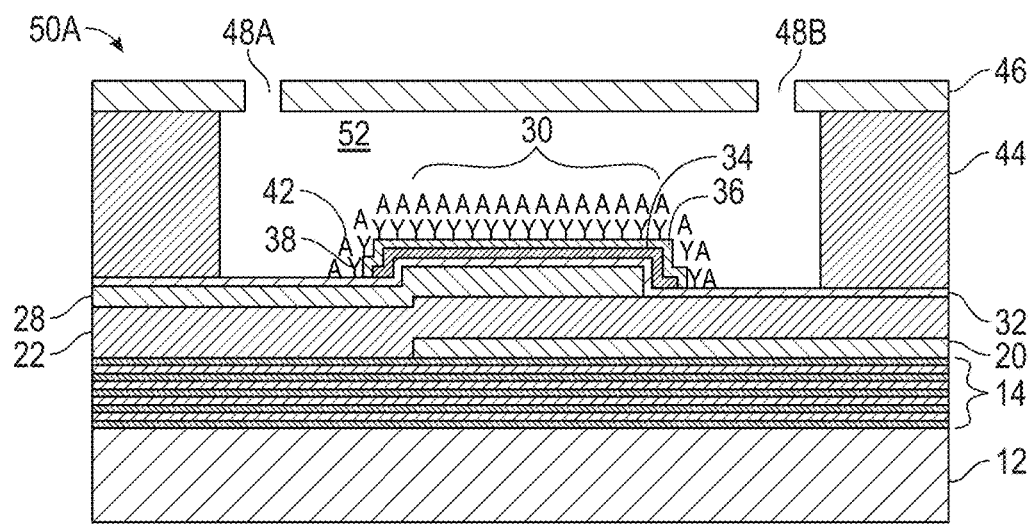
FIG. 8 is a schematic cross-sectional view of the microfluidic device of FIG. 7, following supply of liquid to the microfluidic channel to cause a target species to be bound to the functionalization (e.g., specific binding) material.

FIG. 8 is a schematic cross-sectional view of the microfluidic device 50A of FIG. 7, following supply of liquid to the microfluidic channel 52 (i.e., through one or both fluidic ports 48A, 48B to cause a target species 42 to be bound to the functionalization material 38. In certain embodiments, the functionalization material 38 comprises specific binding material that is selected to specifically bind the target species 42. In operation, the bulk acoustic wave MEMS resonator device is driven with a shear radio frequency to detect the frequency shift of the bound target species (or analyte) 42.

In the microfluidic device 50A illustrated in FIGS. 7 and 8, the interface layer 34, SAM 36, and functionalization material 38 cover the entire active region 30. In alternative embodiments, an interface layer, a SAM, and functionalization material may be arranged over less than an entirety of an active region.

Figure 9:
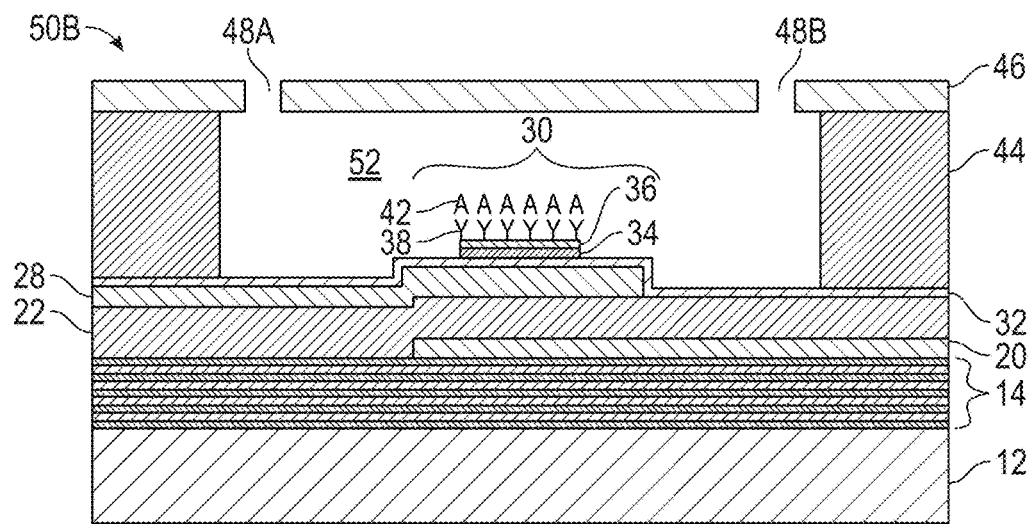
FIG. 9 is a schematic cross-sectional view of a microfluidic device incorporating a bulk acoustic wave MEMS resonator device according to FIG. 1, with top side electrode and piezoelectric material surfaces overlaid with a hermeticity layer, with an interface layer patterned over a portion of the hermeticity layer to cover less than an entirety of an active region of the MEMS resonator device, and with functionalization (e.g., specific binding) material arranged over the interface layer, according to one embodiment of the present disclosure

FIG. 9 is a schematic cross-sectional view of a microfluidic device 50B incorporating a bulk acoustic wave MEMS resonator device according to FIG. 1, with functionalization (e.g., specific binding) material 38, a SAM 36, and an interface layer 34 arranged over less than an entirety of an active region 30. The MEMS resonator device includes a substrate 12, an acoustic reflector 14, a bottom side electrode 20 arranged below a portion of the piezoelectric material 22, and a top side electrode 28 arranged over a portion of the piezoelectric material 22, wherein an area in which the piezoelectric material 22 is arranged between overlapping portions of the top side electrode 28 and the bottom side electrode 20 defines the active region 30. A hermeticity layer 32 is arranged over (e.g., the entirety of) the top side electrode 28 and the piezoelectric material 22. After formation of the hermeticity layer 32, an interface layer 34 is patterned over a portion of the hermeticity layer 32, overlying a portion (but less than an entirety) of the active region 30. Thereafter, a SAM 36 is formed over the interface layer 34. Following formation of the SAM 36, walls 44 may be formed to define lateral boundaries of a microfluidic channel 52 containing the active region 30 (e.g., with the walls 44 being laterally displaced from the active region 30), and the functionalization material 38 is applied to the SAM 36 (e.g., by microarray spotting). Thereafter, a cover 46 is applied to top surfaces of the walls 44, with the cover 46 defining fluidic ports 48A, 48B suitable to permit fluid (e.g., liquid) containing a target species 42 to be introduced into the microfluidic channel 52. As shown in FIG. 9, the target species 42 is bound to the functionalization material 38, such as may occur after fluid containing the target species 42 is flowed into the microfluidic channel 52 to contact the functionalization material 38. The use of a functionalization material 38 covering less than an entirety of the active region 30 may be beneficial to adjust response sensitivity and/or detection limit of the microfluidic device 50B.

In certain embodiments, a patterned blocking layer (e.g., including one or more non-oxide thin films such as silicon nitride [$Si_3N_4$] or silicon carbide [SiC]; or organic materials such as SU-8, photoresist, polyimide, parylene, or poly (ethylene glycol)) may be arranged over at least a portion of an interface layer, whereby presence of the patterned blocking material renders a portion of the interface layer unavailable to receive a SAM.

Figure 10:
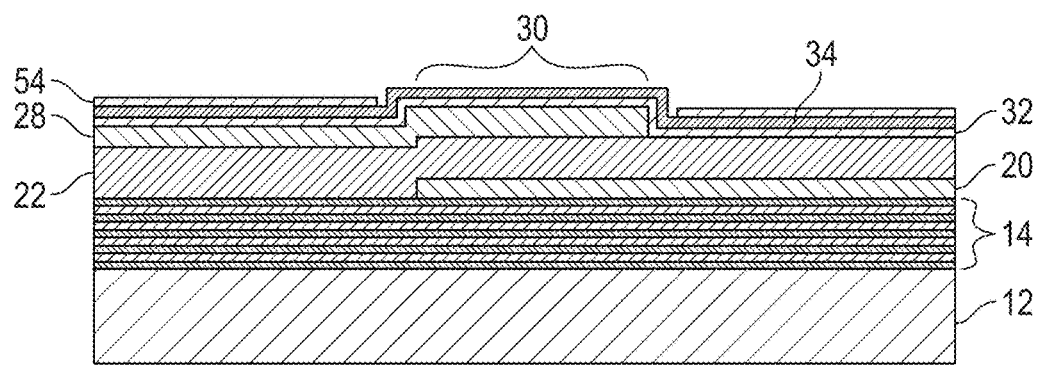
FIG. 10 is a schematic cross-sectional view of a MEMS resonator device portion according to FIG. 1, following deposition of hermeticity and interface layers over top side electrode and piezoelectric material surfaces, with a blocking material layer patterned over portions of the interface layer non-coincident with the active region of the MEMS resonator device, according to one embodiment of the present disclosure.

FIG. 10 is a schematic cross-sectional view of a MEMS resonator device portion according to FIG. 1 (including a substrate 12, an acoustic reflector 14, a piezoelectric material 22, bottom and top side electrodes 20, 28), following deposition of a hermeticity layer 32 and an interface layer 34 over surfaces of the top side electrode 28 and the piezoelectric material 22, and following patterning of a blocking material layer 54 over portions of the interface layer 34 non-coincident with an active region 30 of the MEMS resonator device, according to one embodiment of the disclosure. The zone and area of functionalization is ultimately determined by areas of the interface layer 34 exposed by the patterned blocking material layer 54. The interface layer 34 preferably comprises a hydroxylated oxide surface, or gold or another noble metal, suitable for receiving a SAM (not shown). In certain embodiments, the hermeticity layer 32 and the interface layer 34 may be provided over substantially the entire piezoelectric material 22 and/or the entire MEMS resonator device, but less than an entirety of the piezoelectric material 22 is overlaid with interface layer material that is available to receive a self-assembled monolayer, due to presence of the blocking material layer 54 overlying portions of the interface layer 34. In certain embodiments, the blocking material layer 54 includes at least one of $Si_3N_4$, SiC, Au, photoresist, polyimide, or parylene. Following fabrication of the piezoelectric material 22 and electrodes 20, 28, the hermeticity layer 32 and the interface layer 34 may be deposited by any suitable methods disclosed herein. Thereafter, a patterning technique such as photolithography and selective etching may be used to pattern the blocking material layer 54 with a high degree of precision over portions of the interface layer 34. Following application of the blocking material layer 54, only a central portion of the interface layer 34 proximate to the active region 30 is available to receive a SAM (not shown).

Figure 11:
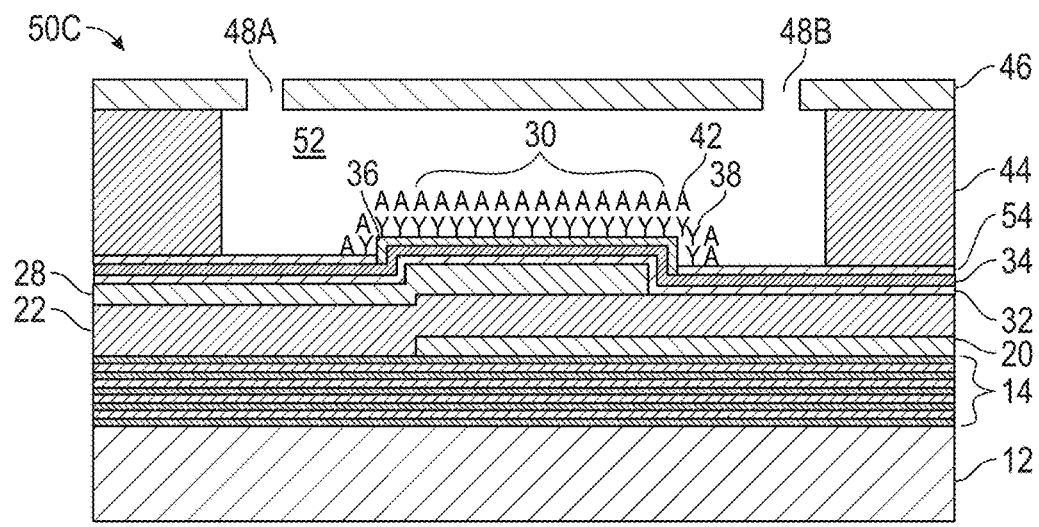
FIG. 11 is a schematic cross-sectional view of a microfluidic device incorporating a bulk acoustic wave MEMS resonator device according to FIG. 10, with a self-assembled monolayer and a functionalization (e.g., specific binding) material arranged over the interface layer coincident with the entire active region of the MEMS resonator device, with a target species bound to the functionalization material, and with walls defining lateral boundaries and with a cover or cap layer defining an upper boundary of a microfluidic channel containing the active region, according to one embodiment of the present disclosure.

FIG. 11 is a schematic cross-sectional view of a microfluidic device 50C incorporating a bulk acoustic wave MEMS resonator device according to FIG. 10, with a self-assembled monolayer (SAM) 36 and a functionalization (e.g. specific binding) material 38 arranged over a central portion of the interface layer 34 overlapping an entire active region 30 of the MEMS resonator device. The MEMS resonator device further includes a substrate 12, an acoustic reflector 14, a bottom side electrode 20 and a top side electrode 28 adjacent to a piezoelectric material 22, and hermeticity layer 32 arranged over surfaces of the piezoelectric material 22 and the top side electrode 28. Walls 44 are laterally displaced from the active region 30 extend upward from a blocking material layer 54, and define lateral boundaries of a microfluidic channel 52 containing the active region 30. A cover 46 is arranged over top surfaces of the walls 44 and defines fluidic ports 48A, 48B suitable to permit fluid (e.g., liquid) containing a target species 42 to be introduced into the microfluidic channel 52. As shown in FIG. 11, the target species 42 is bound to the functionalization material 38, such as may occur after fluid containing the target species 42 is flowed into the microfluidic channel 52 to contact the functionalization material 38.

In other embodiments, an interface layer is patterned over a SAM, or is otherwise available to receive a SAM, over only a portion of an active region, to permit a SAM and functionalization material applied over the interface layer to overlap only a portion of the active region.

Figure 12:
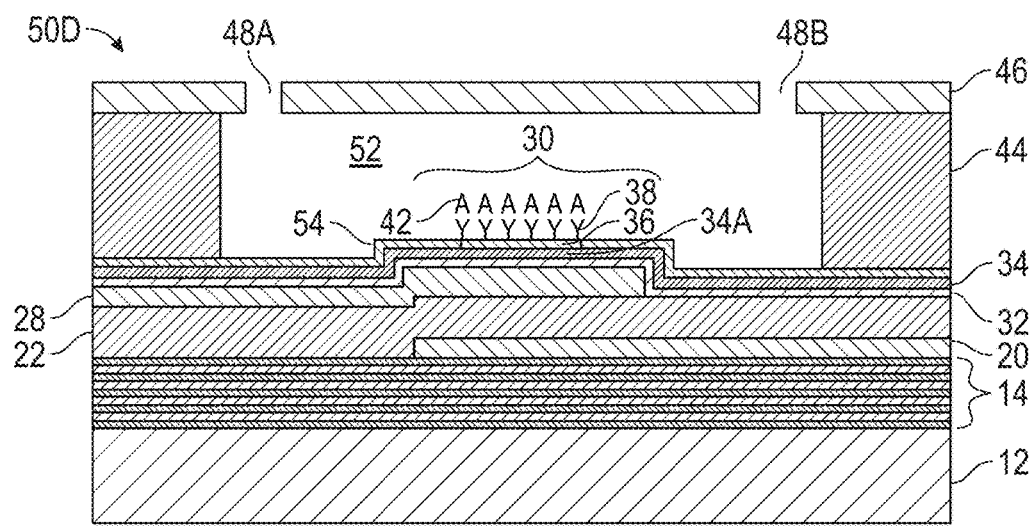
FIG. 12 is a schematic cross-sectional view of a microfluidic device incorporating a bulk acoustic wave MEMS resonator device similar to the device of FIG. 10, with a blocking material layer patterned over the interface layer including portions coincident with the active region, with a self-assembled monolayer and a functionalization (e.g., specific binding) material arranged over a central portion of the active region, with a target species bound to the functionalization material, and with walls defining lateral boundaries and with a cover or cap layer defining an upper boundary of a microfluidic channel containing the active region, according to one embodiment of the present disclosure.

FIG. 12 is a schematic cross-sectional view of a microfluidic device 50D incorporating a bulk acoustic wave MEMS resonator device similar to the device of FIG. 10, but with a blocking material layer 54 patterned over the interface layer 34 including portions coincident with (i.e., overlapping) the active region 30. Only a central portion 34A of the interface layer 34 includes an upper surface available to receive a self-assembled monolayer (SAM) 36, such that the SAM 36 and overlying functionalization (e.g., specific binding) material 38 are arranged over only a portion of the active region 30. The MEMS resonator device further includes a substrate 12, an acoustic reflector 14, a bottom side electrode 20 and a top side electrode 28 adjacent to a piezoelectric material 22, and a hermeticity layer 32 arranged over the piezoelectric material 22 and the top side electrode 28. Walls 44 are laterally displaced from the active region 30, extend upward from the blocking material layer 54, and define lateral boundaries of a microfluidic channel 52 containing the active region 30. A cover 46 is arranged over top surfaces of the walls 44 and defines fluidic ports 48A, 48B suitable to permit fluid (e.g., liquid) containing a target species 42 to be introduced into the microfluidic channel 52. As shown in FIG. 12, the target species 42 is bound to the functionalization material 38, such as may occur after fluid containing the target species 42 is flowed into the microfluidic channel 52 to contact the functionalization material 38.

Figure 13:
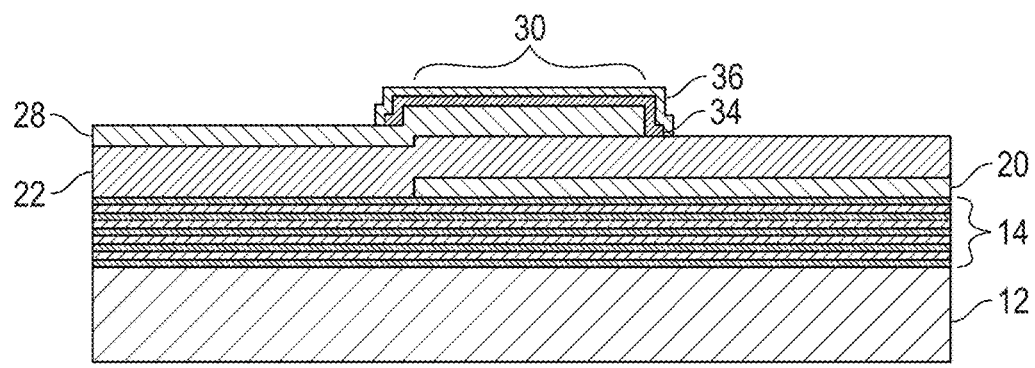
FIG. 13 is a schematic cross-sectional view of a portion of a MEMS resonator device including an inert (e.g., noble metal) top side electrode, and including an interface layer and a self-assembled monolayer arranged over the top side electrode coincident with an active region of the MEMS resonator device, according to one embodiment of the present disclosure.

FIG. 13 a schematic cross-sectional view of a portion of a MEMS resonator device including an inert (e.g., noble metal) top side electrode 28 (thereby obviating the need for a hermeticity layer to cover the top side electrode 28), with an interface layer 34 and a self-assembled monolayer (SAM) 36 arranged over the top side electrode 28 coincident with an active region 30 of the MEMS resonator device, according to one embodiment of the present disclosure. The MEMS resonator device further includes a substrate 12, an acoustic reflector 14, and a bottom side electrode 20 adjacent to a piezoelectric material 22. The interface layer 34 may be deposited by any suitable deposition technique disclosed herein (e.g., ALD, CVD, or PVD), preferably in conjunction with one or more masks (e.g., photolithographic masks) to precisely control its placement. The interface layer 34 preferably comprises a material including a hydroxylated oxide surface suitable for attachment of an organosilane-based SAM, or comprises gold or another noble metal suitable for attachment of a thiol-based SAM. After formation of the interface layer 34, the self-assembled monolayer (SAM) 36 may be deposited thereon.

Figure 14:
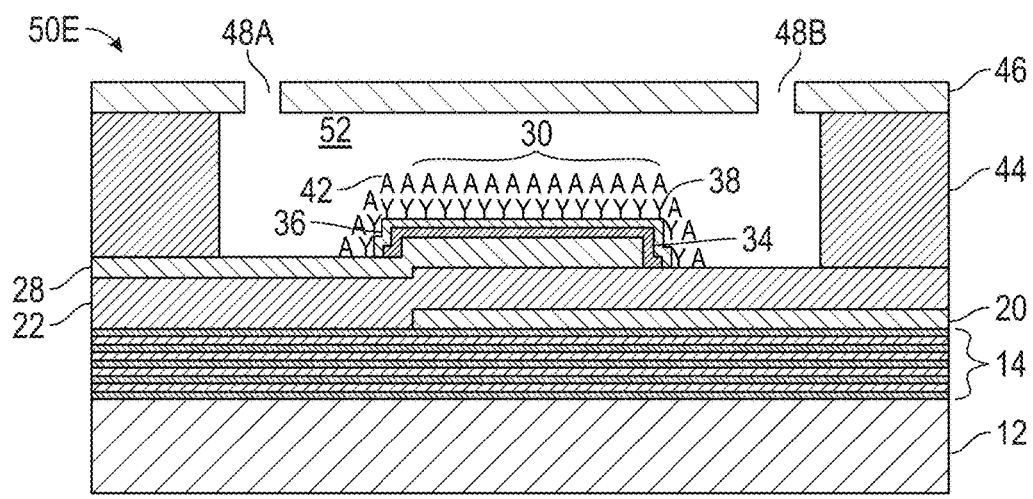
FIG. 14 is a schematic cross-sectional view of a microfluidic device incorporating the bulk acoustic wave MEMS resonator device of FIG. 13, with functionalization (e.g., specific binding) material arranged over the interface layer, with a target species bound to the functionalization material, and with walls and a cover or cap layer defining lateral boundaries and an upper boundary, respectively, of a microfluidic channel containing the active region, according to one embodiment of the present disclosure.

FIG. 14 is a schematic cross-sectional view of a microfluidic device 50E incorporating the bulk acoustic wave MEMS resonator device of FIG. 13. Walls 44 are laterally displaced from the active region 30, extend upward from the piezoelectric material 22 and top side electrode 28, and define lateral boundaries of a microfluidic channel 52 containing the active region 30. A cover 46, arranged over top surfaces of the walls 44, defines a top boundary of the microfluidic channel 52, and defines fluidic ports 48A, 48B suitable to permit fluid (e.g., liquid) containing a target species 42 to be introduced into the microfluidic channel 52. As shown in FIG. 14, functionalization (e.g., specific binding) material 38 is arranged over the SAM 36 and the interface layer 34, and the target species 42 is bound to the functionalization material 38, such as may occur after fluid containing the target species 42 is flowed into the microfluidic channel 52 to contact the functionalization material 38.

Figure 15:
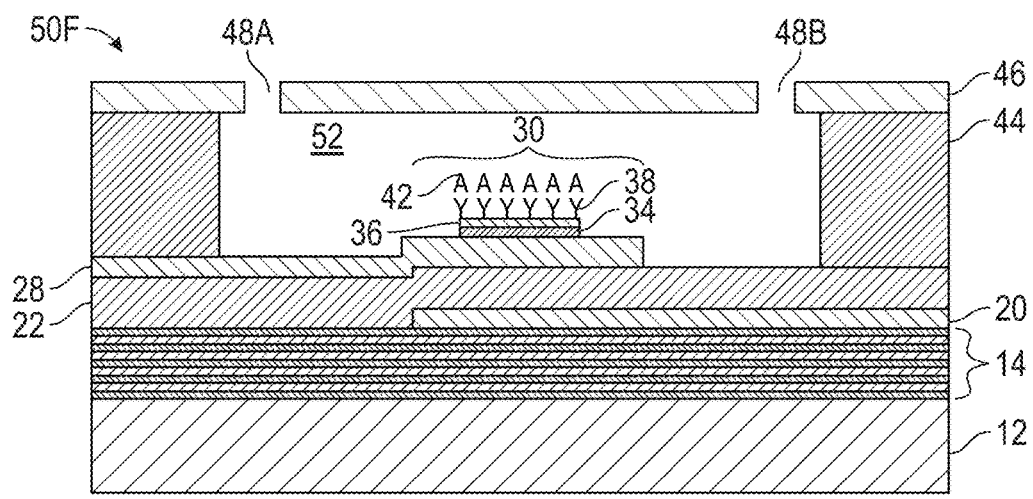
FIG. 15 is a schematic cross-sectional view of a microfluidic device incorporating a bulk acoustic wave MEMS resonator device, with an interface layer and functionalization (e.g., specific binding) material arranged over a central portion of a top electrode coincident with a central portion of an active region, with a target species bound to the functionalization material, and with walls and a cover or cap layer defining lateral boundaries and an upper boundary, respectively, of a microfluidic channel containing the active region, according to one embodiment of the present disclosure.

FIG. 15 is a schematic cross-sectional view of a microfluidic device 50F incorporating a bulk acoustic wave MEMS resonator device, with an interface layer 34, a SAM 36, and a functionalization (e.g., specific binding) material 38 arranged over only a portion of an active region 30 of the MEMS resonator device. The MEMS resonator device further includes a substrate 12, an acoustic reflector 14, and a bottom side electrode 20 and a top side electrode 28 adjacent to a piezoelectric material 22, wherein an area in which the piezoelectric material 22 is arranged between overlapping portions of the top side electrode 28 and the bottom side electrode 20 is considered the active region 30. The interface layer 34 may be deposited by any suitable deposition technique disclosed herein (e.g., ALD, CVD, or PVD), preferably in conjunction with one or more masks (e.g., photolithographic masks) to precisely control its placement. The interface layer 34 preferably comprises a material including a hydroxylated oxide surface suitable for attachment of an organosilane-based SAM, or comprises gold or another noble metal suitable for attachment of a thiol-based SAM. Walls 44 are laterally displaced from the active region 30, extend upward from the piezoelectric material 22 and top side electrode 28, and define lateral boundaries of a microfluidic channel 52 containing the active region 30. A cover 46 arranged over top surfaces of the walls 44 defines a top boundary of the microfluidic channel 52, and defines fluidic ports 48A, 48B suitable to permit fluid (e.g., liquid) containing a target species 42 to be introduced into the microfluidic channel 52. As shown in FIG. 15, functionalization material 38 is arranged over the SAM 36 and the interface layer 34, and the target species 42 is bound to the functionalization material 38, such as may occur after fluid containing the target species 42 is flowed into the microfluidic channel 52 to contact the functionalization material 38.

Figure 16:
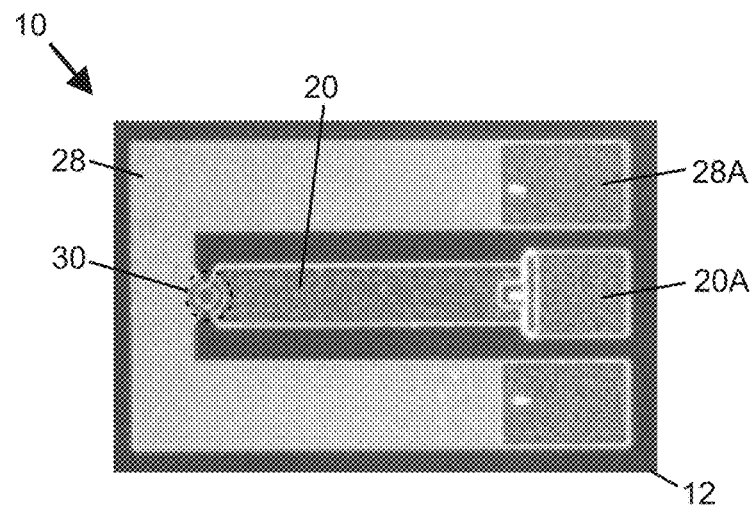
FIG. 16 is a top plan view photograph of a bulk acoustic wave MEMS resonator device suitable for receiving a hermeticity layer, an interface layer, a self-assembled monolayer, and functionalization (e.g. specific binding) material as disclosed herein.

FIG. 16 is a top plan view photograph of a bulk acoustic wave MEMS resonator device 10 (consistent with the portion of a device 10 illustrated in FIG. 1) suitable for receiving an optional hermeticity layer, an interface layer, a self-assembled monolayer, and functionalization (e.g., specific binding) material as disclosed herein. The MEMS resonator device 10 includes a piezoelectric material (not shown) arranged over a substrate 12, a bottom side electrode 20 arranged under a portion of the piezoelectric material, and a top side electrode 28 arranged over a portion of the piezoelectric material, including an active region 30 in which the piezoelectric material is between overlapping portions of the top side electrode 28 and the bottom side electrode 20. Externally accessible contacts 20A, 28A are in electrical communication with the bottom side electrode 20 and the top side electrode 28, respectively. After portions of the MEMS resonator device 10 is overlaid with an interface layer, a self-assembled monolayer, and functionalization (e.g., specific binding) material as disclosed herein, the device 10 may be used as a sensor and/or incorporated into a microfluidic device. If desired, multiple MEMS resonator devices 10 may be provided in an array on a single substrate 12.

Figure 17:
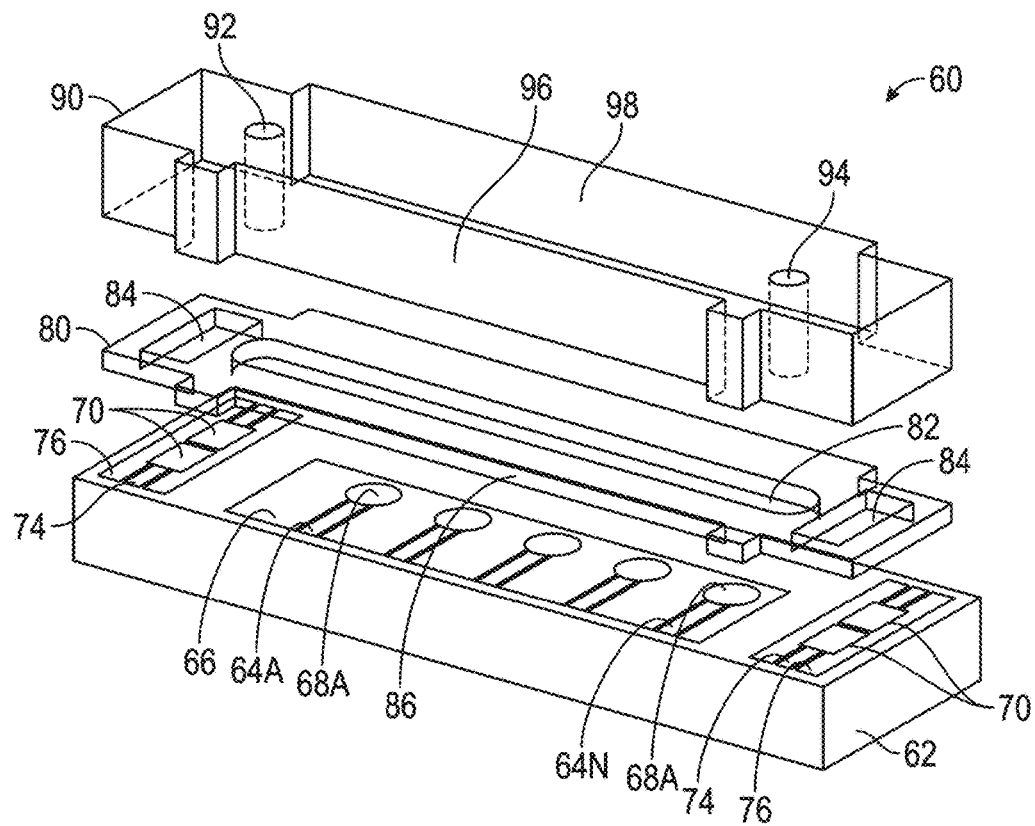
FIG. 17 is a perspective assembly view of a microfluidic device incorporating a substrate with multiple bulk acoustic wave MEMS resonator devices as disclosed herein, an intermediate layer defining a channel containing active regions of the MEMS resonator devices, and a cover or cap layer.

FIG. 17 is a perspective assembly view of a microfluidic device 60 incorporating a substrate 62 with multiple bulk acoustic wave MEMS resonator devices, an intermediate layer 80 defining a central microfluidic channel 82 registered with active regions 68A-68N of the MEMS resonator devices, and a cover or cap layer 90 arranged to cover the intermediate layer 80. Top central portions of the substrate 62, which includes an acoustic reflector (not shown) and a piezoelectric material (not shown), include a top side electrode 66 and bottom side electrodes 64A-64N. Regions in which the foregoing electrodes overlap one another and sandwich the piezoelectric material embody active regions 68A-68N. Any suitable number of active regions 68A-68N may be provided and fluidically arranged in series or parallel, although five active regions are illustrated in FIG. 17. Top peripheral (or top end) portions of the substrate 62 further include reference top side electrodes 76 and reference bottom side electrodes 74 in communication with reference overlap regions 70. Such reference overlap regions 70 are not exposed to fluid, and are present to provide a basis for comparing signals obtained from the active regions 68A-68N exposed to fluid within the central microfluidic channel 82. The substrate 62 is overlaid with the intermediate (e.g., wall-defining) layer 80, wherein the central microfluidic channel 82 is intended to receive fluid, and defines peripheral chambers 84 arranged to overlie the reference overlap regions 70 in a sealed fashion. The intermediate layer 80 may be formed of any suitable material such as SU-8 negative epoxy resist, other photoresist material, or laser-cut "stencil" layers of thin polymeric materials optionally including one or more self-adhesive surfaces (e.g., adhesive tape), etc. The intermediate layer 80 further includes a lateral inset region 86 that enables lateral portions of the top side electrode 66 and bottom side electrodes 64A-64N to be accessed upon assembly of the microfluidic device 60. The cover or cap layer 90 includes a lateral inset region 96 registered with the lateral inset region 86 of the intermediate layer 80, and includes microfluidic ports 92, 94 accessible along a top surface 98 and registered with end portions of the central microfluidic channel 82 defined in the intermediate layer 80 to permit fluid (e.g., liquid) to be supplied to the central microfluidic channel 82 over the active regions 68A-68N. Preferably, at least the electrodes 64A-64N, 66 are overlaid with a hermeticity layer, an interface layer, a self-assembled monolayer, and functionalization (e.g., specific binding) material as disclosed herein. Microfluidic devices according to other configurations may be provided, as will be recognized by those skilled in the art upon review of the present disclosure.

Figure 18:
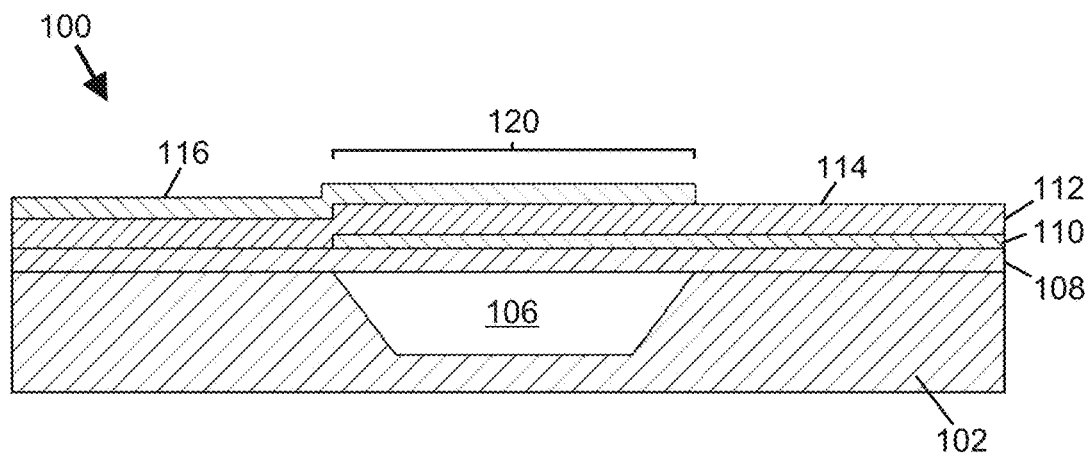
FIG. 18 is a schematic cross-sectional view of a film bulk acoustic wave resonator (FBAR) structure usable in devices according to certain embodiments, with the FBAR structure including an inclined c-axis hexagonal crystal structure piezoelectric material, a substrate defining a cavity covered by a support layer, and an active region registered with the cavity with a portion of the piezoelectric material arranged between overlapping portions of a top side electrode and a bottom side electrode.

FIG. 18 is a schematic cross-sectional view of a film bulk acoustic wave resonator (FBAR) structure 100 including an active region, with at least portions of the FBAR structure 100 subject to being overlaid with an interface layer and a self-assembled monolayer (SAM) suitable for receiving a functionalization material (e.g., specific binding or non-specific binding material), according to one embodiment. The FBAR structure 100 includes a substrate 102 (e.g., silicon or another semiconductor material) defining a cavity 106 that is covered by a support layer 108 (e.g., silicon dioxide). A bottom side electrode 110 is arranged over a portion of the support layer 108, a piezoelectric material layer 112, preferably embodying inclined c-axis hexagonal crystal structure piezoelectric material (e.g., AlN or ZnO), is arranged over the bottom side electrode 110 and the support layer 108, and a top side electrode 116 is arranged over at least a portion of a top surface 114 of the piezoelectric material layer 112. A portion of the piezoelectric material layer 112 arranged between the top side electrode 116 and the bottom side electrode 110 embodies an active region 120 of the FBAR structure 100. The active region 120 is arranged over and registered with the cavity 106 disposed below the support layer 108. The cavity 106 serves to confine acoustic waves induced in the active region 120 by preventing dissipation of acoustic energy into the substrate 102, since acoustic waves do not efficiently propagate across the cavity 106. In this respect, the cavity 106 provides an alternative to the acoustic reflector 14 illustrated in FIGS. 1 and 3-15. Although the cavity 106 shown in FIG. 18 is bounded from below by a thinned portion of the substrate 102, in alternative embodiments at least a portion of the cavity 106 may extend through an entire thickness of the substrate 102. Steps for forming the FBAR structure 100 may include defining the cavity 106 in the substrate 102, filling the cavity 106 with a sacrificial material (not shown) optionally followed by planarization of the sacrificial material, depositing the support layer 108 over the substrate 102 and the sacrificial material, removing the sacrificial material (e.g., by flowing an etchant through vertical openings defined in the substrate 102 or the support layer 108, or lateral edges of the substrate 102), depositing the bottom side electrode 110 over the support layer 108, growing (e.g., via sputtering or other appropriate methods) the piezoelectric material layer 112, and depositing the top side electrode 116.

As will be recognized by one skilled in the art upon review of the present disclosure, in certain embodiments the FBAR structure 100 of FIG. 18 may be substituted for solidly mounted BAW structures disclosed in FIGS. 1 and 3-15, with at least portions of the BAW structures being overlaid with an interface layer and a self-assembled monolayer suitable for receiving a functionalization material (e.g., specific binding or non-specific binding material).

Those skilled in the art will recognize improvements and modifications to the preferred embodiments of the present disclosure. All such improvements and modifications are considered within the scope of the concepts disclosed herein and the claims that follow.

What is claimed is:

1. A micro-electrical-mechanical system (MEMS) resonator device comprising:
   a substrate;
   a bulk acoustic wave resonator structure arranged over at least a portion of the substrate, the bulk acoustic wave resonator structure including a piezoelectric material, a top side electrode arranged over a portion of the piezoelectric material, and a bottom side electrode arranged between the piezoelectric material and the substrate, wherein a portion of the piezoelectric material is between the top side electrode and the bottom side electrode to form an active region; an interface layer arranged over at least a portion of the active region, wherein less than an entirety of the piezoelectric material is overlaid with interface layer material that is available to receive a self-assembled monolayer (SAM); and
   the self-assembled monolayer arranged over at least a portion of the interface layer.

2. The MEMS resonator device of claim 1, wherein the interface layer comprises a hydroxylated oxide surface, and the self-assembled monolayer comprises an organosilane material.

3. The MEMS resonator device of claim 1, wherein the interface layer comprises gold or another noble metal, and the self-assembled monolayer comprises a thiol material.

4. The MEMS resonator device of claim 1, wherein the interface layer is arranged over less than an entirety of the piezoelectric material.

5. The MEMS resonator device of claim 1, further comprising a patterned blocking layer arranged over at least one portion of the interface layer.

6. The MEMS resonator device of claim 5, wherein the patterned blocking layer comprises at least one of silicon nitride, silicon carbide, photoresist, SU-8, polyimide, parylene, or poly (ethylene glycol).

7. The MEMS resonator device of claim 1, further comprising at least one functionalization material arranged over at least a portion of the self-assembled monolayer, wherein at least a portion of the at least one functionalization material is registered with the active region.

8. The MEMS resonator device of claim 1, wherein the top side electrode comprises a non-noble metal, and the MEMS resonator device further comprises a hermeticity layer arranged between the interface layer and the top side electrode.

9. The MEMS resonator device of claim 8, wherein the hermeticity layer comprises an oxide, a nitride, or an oxynitride dielectric material, and the hermeticity layer comprises a water vapor transmission rate of no greater than 0.1 ($g/m^2/day$).

10. The MEMS resonator device of claim 1, wherein the piezoelectric material comprises a hexagonal crystal structure piezoelectric material that comprises a c-axis having an orientation distribution that is predominantly non-parallel to normal of a face of the substrate.

11. A sensor comprising the MEMS resonator device of claim 1.

12. A fluidic device comprising the MEMS resonator device of claim 7, and a fluidic passage arranged to conduct a liquid to contact the at least one functionalization material.

13. A method for biological or chemical sensing, the method comprising:
   supplying a fluid containing a target species into the fluidic passage of a fluidic device according to claim 12, wherein said supplying is configured to cause at least some of the target species to bind to the at least one functionalization material;
   inducing a bulk acoustic wave in the active region; and
   sensing a change in at least one of a frequency property, a magnitude property, or a phase property of the bulk acoustic wave resonator structure to indicate at least one of presence or quantity of target species bound to the at least one functionalization material.

14. A micro-electrical-mechanical system (MEMS) resonator device comprising:
   a substrate;
   a bulk acoustic wave resonator structure arranged over at least a portion of the substrate, the bulk acoustic wave resonator structure including a piezoelectric material, a top side electrode arranged over a portion of the piezoelectric material, and a bottom side electrode arranged between the piezoelectric material and the substrate, wherein a portion of the piezoelectric material is arranged between the top side electrode and the bottom side electrode to form an active region;
   a self-assembled monolayer arranged over at least a portion of the active region; and
   at least one functionalization material arranged over at least a portion of the self-assembled monolayer, wherein less than an entirety of the piezoelectric material is overlaid with the at least one functionalization material.

15. A method for fabricating a micro-electrical-mechanical system (MEMS) resonator device, the method comprising:
   forming a bulk acoustic wave resonator structure including a piezoelectric material, a top side electrode arranged over a portion of the piezoelectric material, and a bottom side electrode arranged between the piezoelectric material and a substrate, wherein a portion of the piezoelectric material is arranged between the top side electrode and the bottom side electrode to form an active region;
   depositing an interface layer over at least a portion of the active region, wherein less than an entirety of the piezoelectric material is overlaid with interface layer material that is available to receive a self-assembled monolayer (SAM); and
   forming a self-assembled monolayer over at least a portion of the interface layer, wherein at least a portion of the self-assembled monolayer is arranged over the active region.

16. The method of claim 15, further comprising applying a patterned mask over at least a portion of the bulk acoustic wave resonator structure prior to the depositing of the interface layer.

17. The method of claim 15, further comprising depositing at least one functionalization material over at least a portion of the self-assembled monolayer, wherein the at least one functionalization material is registered with at least a portion of the active region.

18. The method of claim 15, wherein the top side electrode comprises a non-noble metal, and the method further comprises depositing a hermeticity layer between at least portions of the interface layer and the top side electrode, wherein the hermeticity layer comprises an oxide, a nitride, or an oxynitride dielectric material, and wherein the hermeticity layer comprises a water vapor transmission rate of no greater than 0.1 (g×mm)/(m$^2$×day).

19. The method of claim 15, further comprising depositing a patterned blocking layer over at least one portion of the interface layer.

20. The method of claim 15, further comprising forming at least one wall over a portion of the bulk acoustic wave resonator structure and defining a fluidic passage containing the active region.

* * * * *